United States Patent [19]

Daugalieva et al.

[11] Patent Number: 5,811,100
[45] Date of Patent: *Sep. 22, 1998

[54] COMPOUNDS FOR THE PREVENTION AND TREATMENT OF HELMITH INFECTIONS

[75] Inventors: Emma K. Daugalieva; Arkady V. Nekrasov; Rem V. Petrov; Rakhim M. Khaitov; Ravshan I. Ataullakhanov, all of Moscow, Russian Federation

[73] Assignee: Petrovax, Inc., Deerfield, Mass.

[ * ] Notice: The term of this patent shall not extend beyond the expiration date of Pat. No. 5,503,830.

[21] Appl. No.: 655,282

[22] Filed: May 15, 1996

Related U.S. Application Data

[63] Continuation of Ser. No. 207,486, Mar. 7, 1994, abandoned, which is a continuation-in-part of Ser. No. 120,001, Sep. 10, 1993, Pat. No. 5,503,830.

[51] Int. Cl.$^6$ ............... A61K 39/385; A61K 39/39; A61K 38/00; C07D 243/08
[52] U.S. Cl. ............................. 424/194.1; 424/193.1; 424/184.1; 424/280.1; 514/2; 514/12; 540/575
[58] Field of Search ................ 424/194.1, 184.1, 424/193.1, 280.1; 540/575; 514/2, 12

[56] References Cited

U.S. PATENT DOCUMENTS

| | | | |
|---|---|---|---|
| 3,390,148 | 6/1968 | Austin et al. | 260/240 |
| 3,458,633 | 7/1969 | Austin et al. | 424/246 |
| 3,574,203 | 4/1971 | Conover et al. | 260/243 |
| 3,896,227 | 7/1975 | McFarland et al. | 424/263 |
| 5,503,830 | 4/1996 | Nekrasovc et al. | |

OTHER PUBLICATIONS

Attached Search Chemical Registry.
Allison et al. 1992 in Vaccines: New Approaches to Immunological Problems Ed. R.W. Ellis. pp. 431–449.
Fiszer–Szafarz. 1984. Hgaluronidase Polymorphism Detected by PolyarcylamideGel . . . Analytical Biochem. 143:76–81.
Gupta et al.1993. Adjuants—a balance between toxicity and Adjuvanticity. Vaccine 11 (3):293–306.
Lovgren et al. 1991. The Iscom: An Antigen Delivery System with Built–in Adjuvant Mol.Immunol. 28(3):285–286.
Allison et al. 1991 Immunological Adjuvants:desirable properties and side effects. Mol.Immunol. 28(3):279–284.
Khaitov, Annals Ny Acad. Sci. 685:788–802, 1993.

*Primary Examiner*—Nita Minnifield
*Attorney, Agent, or Firm*—Saliwanchik, Lloyd & Saliwanchik

[57] ABSTRACT

A compound for protecting a vertebrate against infection by helminths comprising hyaluronidase covalently coupled to an immunostimulating carrier, in preferred form, the immunostimulating carrier to which the hyaluronidase is covalently coupled comprising a copolymer of ethylenepiperazine N-oxide and N-ethylacetylethylenepiperazinium bromide (hereafter referred to as "SYNPOL"), and a process for protecting a vertebrate against infection by helminths comprising administration to the vertebrate of a therapeutically effective amount of a compound comprising hyaluronidase covalently coupled to an immunostimulating carrier, preferably SYNPOL, in preferred form, the compound being administered to the vertebrate in the form of a vaccine.

42 Claims, 5 Drawing Sheets

COMPOUNDS FOR THE PREVENTION AND TREATMENT OF HELMITH INFECTIONS

RELATED APPLICATIONS

This is a Continuation application of application Ser. No. 08/207,486, filed Mar. 7, 1994 now abandoned which is a continuation-in-part of application Ser. No. 08/120,001, filed on Sep. 10, 1993 now U.S. Pat. No. 5,503,830.

FIELD OF THE INVENTION

The present invention relates to compositions capable of eliciting an immune response in vertebrates against helminth infections. In particular, the present invention is directed to vaccines which may be used to protect a vertebrate against infection from parasitic helminths.

Helminthic infections are a major cause of morbidity and mortality in both domesticated animals and human populations. Speaking generally, helminths refer to parasitic and non-parasitic species belonging to the phyla platyhelminthes (for example, flukes, tapeworms, and other flatworms) and nematahelminthes (for example, roundworms and their relatives). The following is illustrative of how helminthic infections occur. A helminth species enters the body of a host in the form of eggs or invasive larvae, for example, as a result of the ingestion by the host organism of food containing the eggs or larvae. The helminths then develop, moving slowly through different tissues, blood and/or lymph. Finally, they reach their "preferred" organ, and grow and mature. Eventually, the organ in which they reside is affected adversely.

Control measures rely to a large extent on improvements in hygiene, reduction in vector populations, and chemotherapy. Control measures which focus on hygiene and reduction of vector population have proved to be problematic especially in developing countries where such infections are most prevalent and such control measures are most difficult to implement. Current chemotherapeutic medications all have drawbacks such as high toxicity, the requirement that treatments be repeated and immunosuppressive side-effects. Furthermore, the use of these preparations often results in the parasites' developing resistance to the chemotherapeutic medication. Indeed, nearly every country has documented cases of antihelminthic resistance. For these reasons, as well as the expense of repeated administration of chemotherapeutic compounds, a compound which would not have these drawbacks has been highly sought after.

Since a large variety of helminth species may be found in infected populations, it would desirable to produce a vaccine having a broad spectrum of prophylactic activity. To date, the induction of strong protective host immunity following infection by helminths has been uncommon. The long co-evolutionary experience these parasites have had with their hosts has driven the host-parasite relationship to a level of accommodation that results in chronic or persistent conditions rather than acute infections that typically yield strong specific immunity. For this reason, unlike the situation with most microbial diseases of animals, few vaccines have been available for helminth control, and those which do exist have significant drawbacks.

Of the known methods of producing helminth vaccines, inactivated and living vaccines have the drawback that they are labor-intensive and only weakly immunogenic and they induce side-effects such as a localized inflammation, allergic response, and fever. Furthermore, often the attenuated form used in the vaccine causes a disease similar to that induced by the virulent (wild) forms of the parasite. In addition, the macromolecular carrier proteins used in these vaccine preparations cause a number of immunopathologic side-effects in the vaccinated organism.

The other available class of vaccines comprises genetically engineered antigens. Yet these too are only weakly immunogenic.

In summary, the available types of vaccines are generally ineffective and possess a narrow specificity, being directed against a single parasite.

REPORTED DEVELOPMENTS

A detailed description of helminths in whose life-cycles tissue-migration plays an important part, as well as a discussion of the pathological conditions they cause can be found for example in E. J. Soulsby, *Helminth, Arthropods and Protozoa of Domesticated Animals*, 7th Edition, Lea and Febiger, Philadelphia (1982) and in G. M. Urquhart, "Veterinary Parasitology", *Longman Scientific and Technical, United Kingdom* (1987).

All parasites elicit immune responses, but for many reasons are able to present a moving and sometimes invisible target to the host's immune response, to such an extent that the normal control mechanisms fail and immunological damage instead of immunity often occurs. This in turn frequently leads the host to switch off its ineffective and often counterproductive immune response, thereby resulting in gross pathological changes and immunosuppression.

The structural and antigenic diversity of the parasitic helminths is reflected in the heterogeneity of the specific immune responses they elicit. Parasitic helminths often evade the immune system by masking and shedding their surface antigens and by varying their antigens during their residence in vertebrate hosts. This ability to mask, shed and vary surface antigens is a primary cause of the difficulty experienced heretofore in producing efficacious vaccines against helminths infection.

A review of modern vaccines used in the treatment of parasitic diseases is provided in, J. H. L. Playfair. et al., *The Lancet* 335 (1990): 1263–1266, while a more general discussion of the nature of the immunological response of hosts to parasitic helminths can be found in the article by S. Lloyd and E. J. L. Soulsby in "Parasitology in Focus: Facts and Trends", Ed. H. Mehlhorn, Springer-Verlag (1988) pp. 619–650. As indicated in the Playfair et al. review article and as mentioned hereinabove, since existing helminth control measures are expensive and difficult to implement on a wide scale, there is a strong need for vaccines capable of reducing the intensity and prevalence of helminth infection in host populations.

Prior to the present invention, it was thought unlikely that one antigen alone could confer adequate protection against a wide range of helminth infections based on the difficulties referred to above encountered in producing effective antihelminth vaccines against even specific species. For an overall review of medical and scientific challenges provided by helminths, see A. A. F. Mahmoud, *Science* 246 (1989): 1015–1021. (In addition see also the entries "Parasites, Escape from Immunity", by D. J. Mclaren, and "Parasites, Immunity to" by F. E. G. Cox, in the *Encyclopedia of Immunology*, eds. I. M. Roitt and P. J. Delves, Academic Press, 1992.)

SUMMARY OF THE INVENTION

In accordance with the present invention, there is provided a compound for protecting a vertebrate against infection by helminths comprising hyaluronidase covalently coupled to an immunostimulating carrier. In preferred form, the compound of the present invention is administered to the vertebrate in the form of a vaccine and the immunostimulating carrier to which the hyaluronidase is covalently coupled comprises copolymers of ethylenepiperazine N-oxide and N-ethylacetylethylenepiperazinium bromide (hereafter referred to as "SYNPOL").

The present invention is based in part on the discovery that the enzyme hyaluronidase is produced by larval helminth species in order to penetrate the tissue barriers in the body of a host organism they have infected. In practice, the present invention is capable of eliciting an immune response against hyaluronidase, as produced by the helminths, thereby drastically reducing, if not eliminating, the ability of the helminths to penetrate tissue barriers and thereby infect an animal.

Another aspect of the present invention is the provision of a process for protecting a vertebrate against infection by helminths comprising administration to the vertebrate of a therapeutically effective amount of a compound comprising hyaluronidase covalently coupled to an immunostimulating carrier, preferably synpol. In preferred form, the compound is administered to the vertebrate in the form of a vaccine which includes, in admixture with the compound, synpol. Examples of vertebrates that can be treated in accordance with the present invention include man, cattle, sheep, swine, dogs, horses, cats, goats, buffaloes, camelidae and poultry.

An additional aspect of the present invention is the provision of a process comprising reacting hyaluronidase and an immunostimulating carrier under conditions of time and temperature to covalently couple hyaluronidase and said immunogenic carrier.

The present invention is believed to offer a variety of advantages over prior art techniques for protecting vertebrates from helminthic infections. The compound of the present invention provides protection against infection by those helminth species which utilize hyaluronidase to facilitate their migration within the body of a host organism. Accordingly, the compound of the present invention is efficient against a broad spectrum of helminth species. This is a significant advantage over prior art vaccines which are often limited to protecting a host from only one specific helminth species.

An additional advantage offered by the vaccines of the present invention is that they are strongly immunogenic. Prior art anti-helminth vaccines are often only weakly immunogenic and induce undesirable side effects such as localized inflammation, allergic response, and fever. In addition, prior art vaccines often utilize macromolecular carrier proteins that cause a number of immunopathologic side effects in the vaccinated organism.

These and the various other disadvantages of the prior art anti-helminth vaccines have been overcome by the provision of the compound of the present invention inasmuch as it is able to elicit a strong immunogenic response without the side effects often seen in prior art anti-helminthic vaccine preparations. Furthermore, the compounds of the present invention do not appear to effect development or fertility.

The ability of the vaccine of the present invention to elicit a strong immunogenic response and to provide a broad spectrum of protection against a variety of helminth species offer advantages heretofore unseen in the art of anti-helminthic vaccines.

DETAILED DESCRIPTION OF THE INVENTION

Figure 1:
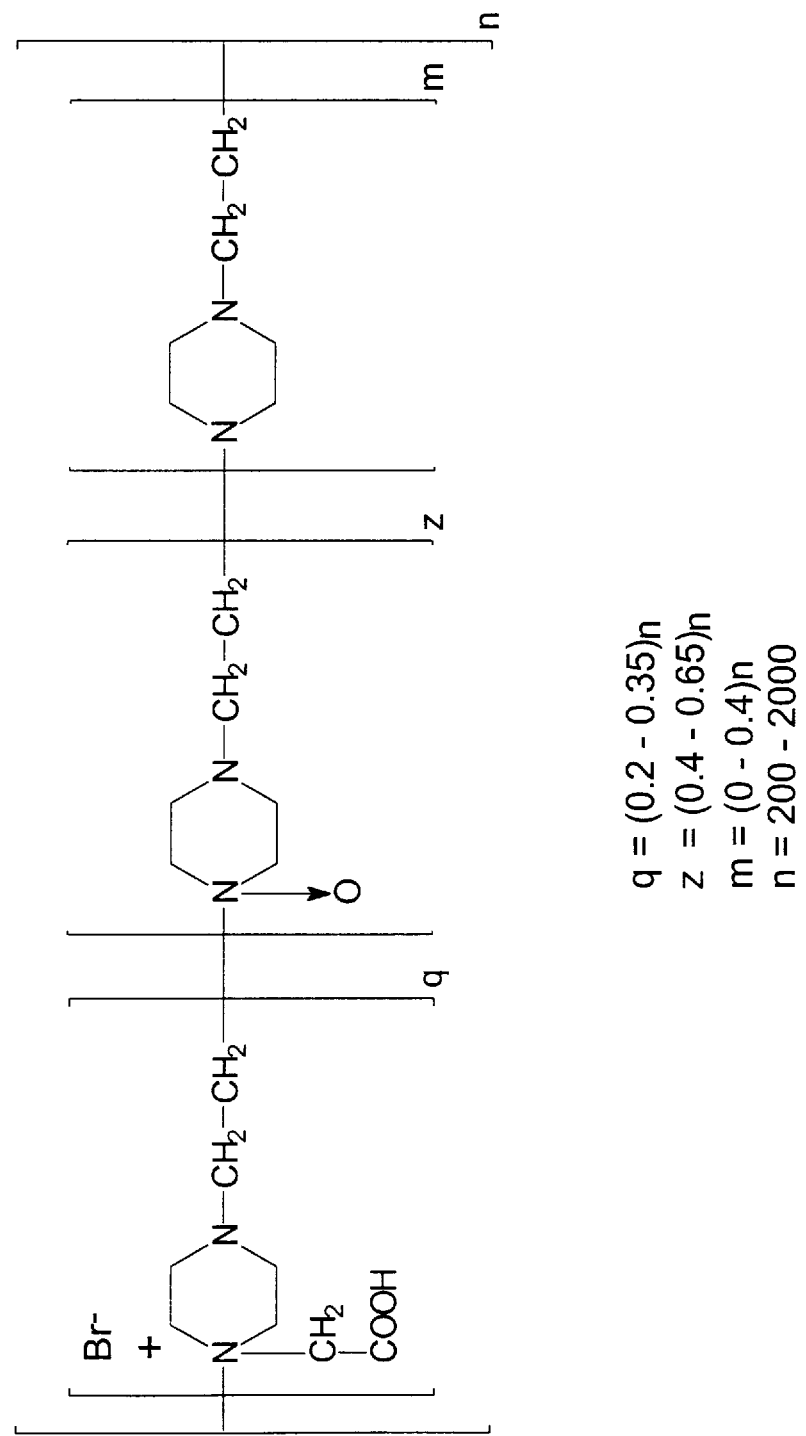
FIG. 1 illustrates the general formula for SYNPOL.

One aspect of the present invention is the provision of a material which comprises the reaction product of hyaluronidase and an immunostimulating carrier.

Hyaluronidase, as the term is used herein, refers to a family of enzymes which hydrolyze naturally occurring polysaccharides, in particular, hyaluronic acid and glycosaminoglycans such as chondroitin sulfates (4-, 6-, D and E). These polymeric substances are essential components of the semisolid gel-like structure of the extracellular matrix. Hyaluronidase cleaves these polymeric substances and therefore is capable of destroying extracellular matrices. A large variety of helminth species produce and use hyaluronidase to hydrolyze the aforementioned components of the host organism's extracellular matrices thereby permitting the helminths to penetrate tissue barriers and migrate within the body of a host organism until they reach a preferred organ where they grow and mature.

The hyaluronidase family includes related enzymes which hydrolyze the aforementioned type substrates. These can be grouped according to their specificity for different linkages within the structure of hyaluronic acid polymer molecules. In particular, the hyaluronidases may be grouped into three primary groups: hyaluronoglucosaminidases, hyaluronoglucuronidases, and glucoronate lyases (B. Fiszer-Szafarz, *Analytical Biochemistry*, vol. 143, p. 76 (1984)).

Native hyaluronidase alone demonstrates extremely weak immunogenicity and does not induce visible anti-hyaluronidase antibody production, even after repeated injections.

Hyaluronidase has been isolated from a variety of sources, including snake and bee venoms, leech saliva, the acrosomal granula of spermatozoa, the lysosomal granula of various cells and from bacterial toxins. Exemplary sources of hyaluronidase that can be used in the practice of the present invention include cattle and sheep testes, helminths, leeches, bee and snake venoms and bacteria.

Bacterial sources of hyaluronidase include, but are not limited to, the following: *Streptococcus millery* (P. F. Unsworth, *J. Clin. Pathology*, (London) 1989, 42(5), 506–510); *Streptococcus pyogenes* (W. L. Hynes and J. J. Ferretti, *Infection and Immunity*, 1989, 57(2), 533–539); *Streptococcus equisimilis* (R. Sting et al., Med. Sci. Res., 1989, vol. 17, No. 17, pp. 723–725); *Clostridium difficicle* (S. V. Seddon et al., *J. Med. Microbiol.*, 1990, v. 31, no. 3, pp. 169–174); *Streptococcus uberis* (P. Schaufuss et al., *Zentralbl. Bakteriol.* FRG, 1989, v. 271, no. 1, pp. 46–53); and *Streptococcus dysgalactiae* (A. Hamai et al., *Agric. Biol. Chem.*, 1989, v. 53, No. 8, pp. 2163–2168). In addition, yeast of the genus candida have also been found to contain hyaluronidase. M. T. Shimizu, *Rev. Microbiol.*, 1988, v. 19, No. 4, pp. 442–445).

In a given species, hyaluronidase generally can be found in monomeric as well as oligomeric forms, with, for example, dimers and tetramers of the same subunit often being present. The amino acid sequence for hyaluronidase produced by *streptococcus pyogenes* bacteriophage has been determined (W. L. Hynes et al., *Infection and Immunity* 57 (1989): 533–539) and bee venom hyaluronidase has recently been sequenced (M. Gmachl et al., *Proc. Natl. Acad. Sci. USA*, 90, 3569–3573 (1993)). It is anticipated that the sequencing and cloning of the genes encoding hyaluronidase will be the basis for recombinant DNA based production of hyaluronidase for use in the practice of the present invention.

A variety of commercially-available preparations of hyaluronidase may be used to prepare the compound of the present invention, including, for example, a bovine preparation of hyaluronidase sold by REANAL CO. (Catalog No. 0705). Polyacrylamide gel electrophoresis (PAGE) of the hyaluronidase obtained from this source indicates the presence of a major protein band having an approximate molecular weight of 63 kilodaltons (kDa). There can be used also a material obtained from sheep testes sold by Sigma Chemical Co. (catalog no. H2126). Polyacrylamide gel electrophoresis of the hyaluronidase obtained from this source reveals a major protein band having an approximate molecular weight of approximately 39 kDa. Hyaluronidase may also be obtained from Serva (Catalog No. 25119 and Catalog No. 25121).

While the hyaluronidase preparations obtained from various commercial sources differ with regards to the predominate protein species present as evidenced by PAGE, it has been found that the various commercial preparations of hyaluronidase are all enzymatically active and are also immunologically cross-reactive with each other. In addition, practically all preparations investigated contain at least traces of a protein species having a molecular weight of approximately 60–69 kDa and one cannot exclude the possibility that the shorter polypeptide chains present in the reducing conditions used in the PAGE process are assembled under physiological conditions into oligomers of about 60–90 kDa.

It is anticipated that compounds of the present invention utilizing hyaluronidase isolated from both ram and bull testes may offer a combination of particularly desirable immunogenicity, cost effectiveness, and convenience. Purification methods for such hyaluronidases are rather well developed and include the commonly used steps of extraction, precipitation, centrifugation, ultrafiltration, ion exchange, and gel chromatography. The compounds of the present invention utilizing hyaluronidase isolated from sheep or bovine testes provoke an immune response to helminth hyaluronidase. Utilization of hyaluronidase isolated from sheep or bovine testes is also significantly more cost-effective than isolating hyaluronidase from helminth larvae. Hyaluronidase of testicular origin has been found to cleave hyaluronic acid and is also able to recognize chondroitin sulfates. (Bartolucci et al., *Int. J. Tissue React.*, 13(6) (1991), p. 311). Accordingly, particularly preferred embodiments of the compounds of the present invention are made utilizing hyaluronidase obtained from the testicles of rams or bulls. In this regard, it has been found that a hyaluronidase of sheep or bovine origin sold by Sigma Chemical Company is suitable in the practice of the present invention.

It has been observed that the compounds of the resent invention which utilize hyaluronidase obtained from a source other than the animal receiving the treatment of the present invention is often more immunogenic than compounds utilizing hyaluronidase isolated from the species being treated. For example, hyaluronidase isolated from sheep tends to induce a stronger immune response in cattle than hyaluronidase isolated from cattle. For cost effectiveness and convenience in the treatment of sheep and cattle, consideration should be given to use of a compound that is prepared from a mixture of both ram and bull hyaluronidases.

Compounds within the scope of the present invention comprise the reaction product of hyaluronidase, as described above, and an immunostimulating carrier. As the term is used herein, "immunostimulating carrier" refers to a compound which, when combined with a given antigen, provides for a highly immunogenic complex (antigen-immunostimulant) which may effectively immunize even low responding individuals to a given antigen. Examples of immunostimulating carriers which can be used in the practice of the present invention are described in the following publication which includes a discussion of the utilization of synthetic polyions as immunostimulators: Khaitov, R., *Annals New York Academy of Sciences*, 685, 788–802, Jun. 23, 1993. Reference is made in this article to polyoxidonium which is equivalent to Synpol as used in the present invention.

In preferred embodiments, the immunostimulating carrier that is reacted with hyaluronidase is SYNPOL. As used herein, the term "SYNPOL" refers to copolymers of ethylenepiperazine N-oxide and N-ethylacetylethylenepiperazinium bromide, corresponding to the formulae shown below in FIG. 1, where n=200–2000; q=(0.2–0.35)n; z=(0.4–0.65)n; m=(0–0.4)n.

SYNPOL, unlike most other carriers and adjuvants, is non-immunogenic. It is thought that SYNPOL has no recognizable antigenic determinants and, accordingly, does not provoke an immune response thereby avoiding undesirable side effects observed with most other adjuvants and carriers used in vaccine preparations.

In order to identify in a convenient way the various species of SYNPOL one from another, the term "synpol" is used in combination and sequentially with values for each of the aforementioned letters "n", "q", "z", and "m". For example, ethylenepiperazine N-oxide and N-acetylethylenepiperazinium bromide with n=1000, q=0.35, z=0.60, m=0.05 is referred to as "SYNPOL 1000-35/60".

An example of a specific SYNPOL species copolymer used successfully as an immunostimulating carrier in the vaccine embodiments of the present invention will be referred to herein as "SYNPOL 1000-20/50". Synpol having a molecular weight of at least about 15 kDa or greater is preferred in the practice of the present invention with SYNPOL having a molecular weight greater than at least about 30 kDa being especially preferred.

The compound of the present invention can be made by any suitable method which effects the chemical linking of hyaluronidase to the immunostimulating carrier, for example, by covalently coupling hyaluronidase to the immunostimulating carrier. Such covalent bonds can be formed directly between reactive groups on the hyaluronidase and on the immunostimulating carrier or they can be formed through one or more linking groups. As will be seen in examples set forth hereinbelow, a preferred method for preparing the reaction product of hyaluronidase and the preferred immunostimulating carrier of the present invention, that is, SYNPOL, involves use of the azide method. This method involves converting the acid or ester form of SYNPOL to the hydrazide by use of hydrazine and thereafter combining it with hyaluronidase under conditions which produce a reaction product in which hyaluronidase is covalently coupled to SYNPOL. Alternatively, and as also illustrated in the following examples, another preferred method for preparing the reaction product of hyaluronidase and SYNPOL involves the formation of a succinimide ether of synpol. The succinimide ether is then combined with hyaluronidase under conditions to produce a compound for use in the practice of the present invention.

It is believed that the compound of the present invention will be used most widely to protect vertebrates from infection by helminths. For this purpose, it is preferred that the product of the reaction of a hyaluronidase and an immunostimulating carrier be used in the form of a vaccine. As the term is used herein, "vaccine" refers to a composition which contains the compound of the present invention and which is in a form that is capable of being administered to a vertebrate. Typically, the vaccine comprises a conventional saline or buffered aqueous solution medium in which the compound of the present invention is suspended or dissolved. In this form, the compound of the present invention can be used conveniently to prevent, ameliorate, or otherwise treat a helminth infection.

In preferred form, the vaccine of the present invention additionally includes an adjuvant which can be present in either a minor or major proportion relative to the compound of the present invention. The term "adjuvant" as used herein refers to non-specific stimulators of the immune response which when combined with the vaccine of the present invention, provide for an enhanced immune response. A variety of adjuvants can be used. Examples include complete and incomplete Freund's adjuvant, aluminum hydroxide, and modified muramyldipeptide. In preferred embodiments of the present invention, SYNPOL is used as an adjuvant in admixture with the compound of the present invention.

As mentioned herein above, the compounds of the present invention are intended to be used to protect vertebrates species from helminthic infections. Examples of vertebrates that can be treated in accordance with the present invention include man and various domesticated animals, including, for example, cattle, sheep, swine, dogs, horses, cats, and goats, as well as other equidae, buffaloes, camelidae, and poultry. In particular, it is expected that the compounds of the present invention will be efficacious in the prevention and treatment of parasitic helminth infections in animals which are exposed to helminth species which utilize hyaluronidase.

The compound of the present invention may be administered parenterally by intramuscular, subcutaneous, or intradermal administration. The preferred route of administration for a given organism may be found by reference to the Examples section of the application. Preferred dose ranges may vary given the animal being treated and the most prevalent helminth species in a given environment, but in general, a vaccine dose of about 0.05 mg of protein/kg of animal weight has been found to be effective. Further guidance regarding effective does ranges may be found by referring to the Examples section hereinbelow.

It has been found that the mild conditions which can be preferably utilized for covalently coupling hyaluronidase to SYNPOL do not affect the antigenic epitopes of hyaluronidase in a significant manner; accordingly, a highly immunogenic compound is obtained. Solid-phase enzyme-linked immunoassays (ELISA) have shown that anti-hyaluronidase antibodies can recognize the epitopes of hyaluronidase which have been conjugated to SYNPOL, demonstrating that these epitopes are retained.

It has been found also that the enzymatic site of hyaluronidase is retained after the covalent coupling of hyaluronidase to SYNPOL. In particular, it has been observed that the substrate degradation rate of hyaluronidase alone is substantially identical to the substrate degradation rate of hyaluronidase which has been covalently coupled to SYNPOL. Furthermore, hyaluronidase when coupled to SYNPOL, is significantly more stable than the native enzyme. This has been demonstrated using hyaluronidase enzyme inactivation tests, including thermostability trials and resistance to heparin mediated inhibition.

The enhanced stability of hyaluronidase provided by its conjugation to SYNPOL provides a broad spectrum of other utilities for the compound of the present invention. In addition to its ability to inhibit helminth infections, it is anticipated that the compound of the present invention may be used to elicit an immune response to other pathogens or organisms, for example, those pathogens or organism which make use of hyaluronidase to digest tissue, such as, for example, certain bacteria and their toxins. In addition, the compound of the present invention can be used to block the action or to localize the spreading of venoms containing hyaluronidase (such as bee and snake venoms).

The present invention also includes within its scope methods of using hyaluronidase covalently coupled to SYNPOL to treat fibrosis in vertebrates by administering a composition comprising hyaluronidase covalently bound to SYNPOL.

In addition, the compound of the present invention can be used in cosmetology as the active ingredient in creams and other products used to make skin smoother and more tender. In this regard, it should be noted that materials containing human sperm have been used as skin-care products in Russia. However, the use of such a product is highly limited because of the instability of the hyaluronidase. Since the compound of the present invention is stable, soluble, and non-toxic, it has immediate applications in this area, and indeed investigations of it uses in this regard have been carried out. The present invention also includes within its scope the use of hyaluronidase covalently bound to SYNPOL as a spreading factor to increase the efficacy of medications. It can also be used to improve diffusion and hasten absorption in medical use, for example, as an ingredient in an antibiotic solution for the treatment of bovine mastitis in veterinary use. In the past, unstabilized hyaluronidase has been used in these contexts (cf. The Merck Index, 8th Edition for example), and accordingly, the stabilized form of hyaluronidase provided by the present invention is expected to provide significant advantages over compositions which use the native form of hyaluronidase.

The present invention also includes within its scope the use of hyaluronidase covalently bound to SYNPOL in the following therapeutic contexts where free (unstabilized) hyaluronidase has been shown to have beneficial effects: myocardial infarctions (cf. E. J. Flint et al, *The Lancet*, Apr. 17 (1982) pp.871–874 and also D. Maclean et al, *Science*, vol. 194, pp.199–200 (1976)); improving retinal function (cf. B. S. Winkler et al, *Arch. Opthalmol.* 103 (1985) pp.1743–1746); in combination with cytostatics in the treatment of cancer tumors (G. Baumgartner et al., *J. Exp. Clin. Cancer. Res.* 4 (1985) p.3, and W. Scheithauer et al., *Anticancer Res.*, vol 8, pp.391–395 (1988)); in the management of tuberculous spinal arachnoiditis (cf. M. Gourie-Devi et al., *J. Neurol. Sci.*, vol. 102, pp.105–111 (1991)); for the management of encapsulated brain abscesses in high-risk risk patients (cf. A, Pasaoglu, *Acta Neurochir.*, vol. 100, pp.79–83 (1989)). Furthermore, hyaluronidase has been used in vitro for depolymerizing hyaluronic acid in a cell free system, for instance, or for stimulating hyaluronic acid synthetase in eg. cell-culturing procedures (L. H. Philipson et al, Biochemistry 24 (1985) pp.7899–7906). The present invention also includes within its scope the use of the compound comprising hyaluronidase covalently bound to SYNPOL in these contexts.

In addition, the invention includes within its scope SYNPOL-antigen conjugate vaccines in which the antigen comprises proteins similar to hyaluronidase, for example, vaccines containing as the antigen other enzymes used by pathogens to digest/degrade tissue (including collagenases and proteinases of different specificities).

The invention also includes within its scope the use of SYNPOL coupled with an allergen in order to abolish allergic reactions within a host to a given allergen. Extensive investigation has shown that administering such an antigen-SYNPOL conjugate induces preferentially the production of non-allergic antibody isotypes against the allergen in question. These normal non-pathogenic isotypes compete with the previously existing allergenic one (e.g. IgE immunoglobulins) and specifically abolish the allergy. This method of specific desensitization has been clearly demonstrated and is now in the first stage of clinical trials.

The invention also includes within its scope the use of SYNPOL coupled with the following antigens to enhance the immunogenicity of the coupled antigens, thereby serving to promote the induction of an effective prophylactic immune response: beta-subunit of cholera toxin, hemagglutinin from envelope of types A and B influenza viruses, p. 90 toxin from B. anthracis, the Vi antigen from salmonella, porin protein from the cell wall of E. coli and salmonellae, synthetic fragments of the gp160 env-protein of HIV-1, F(ab)2 fragments of immunoglobulins (in order to induce an anti-idiotype response).

EXAMPLES

The first two examples are illustrative of the preparation of two species of SYNPOL, as identified in the examples.

Example 1

Preparation of SYNPOL 1000-20/50

A three step procedure was used to synthesize a copolymer of ethylenepiperazine N-oxide and N-acetylethylenpiperazinium bromide.

(1) The initial polymer, 1,4-ethylenepiperazine, was synthesized in the first step. For this purpose, the living chain polymerization of 1,4-diazabicyclo[2.2.2]octane was performed according to the following protocol.

10 g of the preliminarily sublimed monomer and 0.05 g of ammonium bromide were sealed in 10 ml glass ampule. A vacuum of residual pressure $5\times10^{-3}$ mm Hg was produced in the ampule using a vacuum pump. The ampule was exposed for 25 hours at 200° C. in a thermostat. Polymer yield was about 100%, M.W. 120,000 (estimated by LALLS-low angle laser light scattering).

(2) The second step was performed to produce the N-oxide of poly-1,4-ethylenepiperazine.

5 g of poly-1,4-ethylenpiperazine (M.W. 120,000, n=1000) were dissolved in 250 ml of 1% acetic acid solution. Then, 4 ml of 30% $H_2O_2$ were added, and oxidation lasted for 36 hours. After ultrafiltration and lyophilization, the N-oxide of poly-1,4-ethylenepiperazine (M.W. 110,000, z=0.5n) was obtained.

(3) The alkylation of the above poly-N-oxide was performed during the third step.

Figure 2:
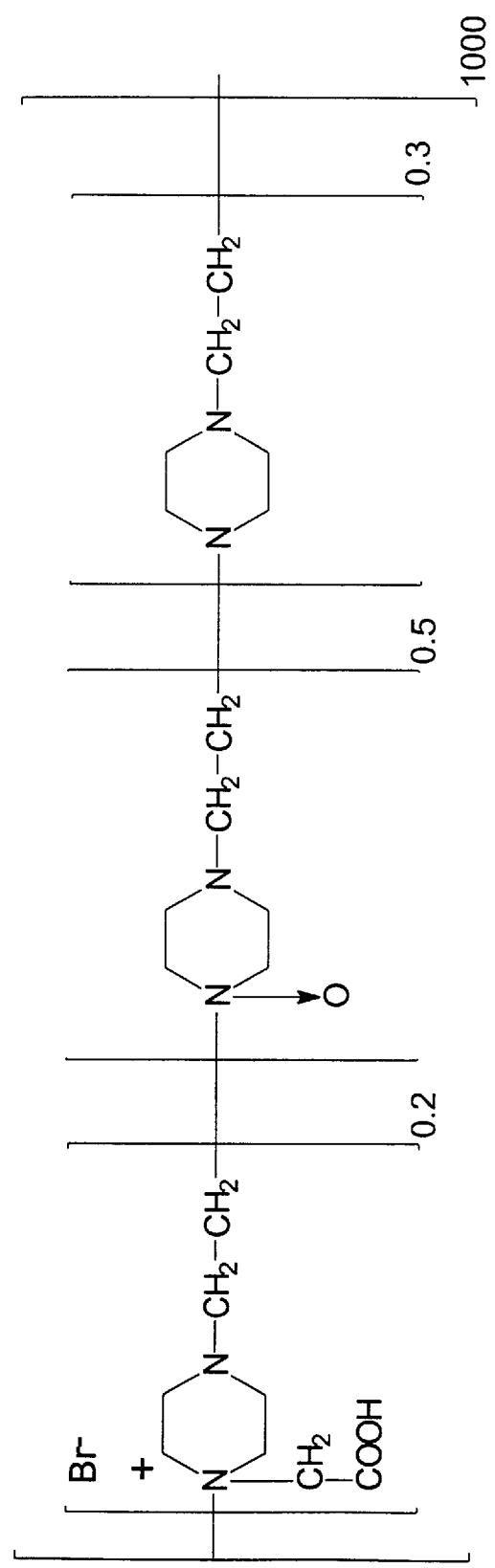
FIG. 2 constitutes the structural formula of SYNPOL which is produced as described in Example 1.

Poly-1,4-ethylenepiperazine N-oxide produced during the second step was dissolved in 125 ml of methanol and 16.5 g of bromoacetic acid were added. The alkylation reaction was carried out for 10 hrs. at 25° C. The solvent was evaporated in a vacuum and the deposit dissolved in water, dialyzed against water for 24 hrs. and dried using lyophilization. Finally, the copolymer of ethylenepiperazine N-oxide and N-acetylethylenepiperazinium bromide of the following formula was obtained (see FIG. 2).

The yield was 95%. The oxidation ratio was estimated by the chromometric (or titanometric titration) method and by the ratio of integral intensities of PMR-spectrum bands in region 2.5–4.5 m.d. The chromometric or titanometric titration method refers to the method of quantitative determination of N-oxide groups reduced by salts of bivalent chrome or trivalent titanium (Brooks, R. T. and P. D. Sternglanz, Anal. Chem., 1959, v. 31, N4, p. 561–565). Oxidation ratio amounted to z=0.5n. Alkylation ratio was determined by IR-spectra (1735 cm band) and PNR-spectra (2.5–4.5 m.d. region) and accounted q=0.2n.

Example 2

Preparation of SYNPOL 200-35/65

A copolymer of ethylenepiperazine N-oxide and N-acetylethylenepiperazinium bromide with M.W. 25,000 (n=200, q=0.35n, z=0.65n) was synthesized using a three step procedure, similar to the one of Example 1.

(1) In the first step, 10 g of the preliminarily sublimed monomer and 0.11 g of ammonium bromide were sealed in a 10 ml glass ampule. Then a vacuum ($5\times10^{-3}$ mm Hg) was produced in the ampule by a vacuum pump, and the ampule was kept at 200° C. for 15 hours. The yield of poly-1,4-ethylenepiperazine was about 100%, M.W. 80,000 (measured by LALLS).

(2) In the second step, the N-oxidation of poly-1,4-ethylenepiperazine was carried out as follows.

5 g of poly-1,4-ethylenepiperazine obtained in the first step were dissolved in 250 ml of 1% acetic acid solution. Then 4.6 ml of 30% $H_2O_2$ was added at 2°–4° C. using gentle agitation. The oxidation lasted for 48 hours. Then after ultrafilter cleaning and lyophilization, the N-oxide of poly-1,4-ethylenepiperazine (M.W. 50,000, z=0.65n) was recovered.

Figure 3:
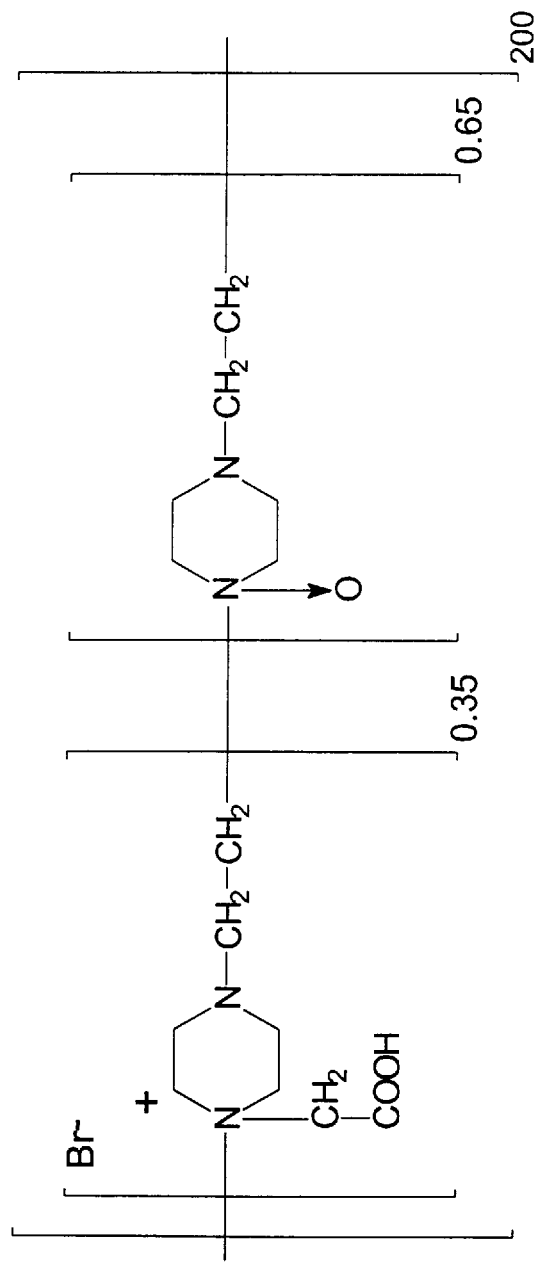
FIG. 3 constitutes the structural formula of SYNPOL which is produced as described in Example 2.

(3) The quantity of poly-1,4-ethylenepiperazine N-oxide produced in the step (2) above was dissolved in 125 ml of methanol and then 16.5 g of bromoacetic acid were added. The reaction of alkylation was carried out at 30° C. for 24 hours. The solvent was evaporated in a vacuum and the resulting deposit obtained was dissolved in water, dialyzed for 24 hours against water, and lyophilized. There was produced a copolymer of ethylenepiperazine N-oxide and N-acetylethylenepiperazinium bromide having the following formula (see FIG. 3).

The yield was 95%. The oxidation and alkylation ratio, both estimated as in Example 1, were z=0.65n and q=0.35n respectively.

The next four examples are illustrative of the preparation of compounds within the scope of the present invention and comprising the reaction products of hyaluronidase and various species of an immunostimulating carrier, namely, SYNPOL of the type which are the subjects of Examples 1 and 2 above.

Example 3

Preparation of the Covalent Conjugate of Hyaluronidase (HYA) with SYNPOL 1000-20/50

A two-step procedure using the azide method was performed in order to synthesize the conjugate of HYA with SYNPOL 1000-20/50.

(1) The first step of the procedure was used to produce the hydrazide of Synpol 1000-20/50'.

A copolymer of ethylenepiperazine N-oxide and N-[ethyl acetyl]ethylenepiperazinium bromide (n=1000, q=0.20, z=0.5) was synthesized according to the method described in Example 1 above except for one change in the third step: ethyl ester of bromoacetic acid was used for alkylation instead of bromoacetic acid. 500 mg of the copolymer were dissolved in 25 ml of methanol. Then 0.2 ml of hydrazine hydrate (0.2 mmol) was added and the reaction continued for 24 hours at 20° C. After the methanol was evaporated, the reaction product was harvested and dissolved in water. Thereafter, ether extraction was performed and the main product isolated by ultrafiltration on hollow fibers (Amicon) and lyophilized.

The content of hydrazide groups in the modified polymer was estimated using a conventional method for primary amino groups determination by 2,4,6-trinitrobenzenesulfonic acid [S. L. Snyder and P. Z. Sobooinsky, "Improved 2,4,6-trinitrobenzenesulfonic acid method for determination of amine," Anal. Biochem., 1975, v. 64, N1, p. 284–288].

(2) In the second step, the reaction of condensation of HYA with the hydrazide of SYNPOL 1000-20/50 was performed in order to produce the covalent protein-polymer conjugate.

To achieve this, 100 mg of the hydrazide of SYNPOL 100-20/50 were dissolved in 4 ml of 1 M HCl. The solution was stirred and cooled down to 0°–2° C., and at the same time 1.15 ml of 3% sodium nitrite solution (0.5 mmol) were added. In 15 minutes, the pH of the activated SYNPOL 1000-20/50 solution was adjusted to 8.5 using 2 M NaOH. Thereafter, a solution of 12 mg of HYA in 10 ml of 0.05 M phosphate buffer (pH 8.5, potassium dihydrogen phosphate, disodium hydrogen phosphate) was added to the aforementioned solution of activated SYNPOL 1000-20/50. The reaction mixture was stirred and cooled (2°–4° C.), and the pH was kept at 8.5 using 2 M NaOH during 12 hours reaction time.

Gel-filtration on Biogel P-100 was used in order to fractionate the components of the reaction mixture and purify the HYA-synpol conjugate. The chromatography column (26×900 mm) was filled with Biogel P-100 available from Biorad Inc. and equilibrated by 0.05 M phosphate buffer with 0.05 M NaCl (pH 7.5). Fractions were eluted using the same buffer and the output was controlled by a flow UV-photometer (226 nm). The conjugate that was obtained was subjected to fluorescence spectroscopy and polyacrylamide gel electrophoresis (PAGE) to estimate the protein content and to analyze the conjugate. It was shown that 1 mg of the conjugate preparation contained 0.10 mg of HYA.

Example 4

Preparation of the Covalent Conjugate of Hyaluronidase (HYA) with SYNPOL 200-35/65

A copolymer of ethylenepiperazine N-oxide and N-acetylethylenepiperazinium bromide (M.W. 25,000, n=200, q=0.35, z=0.65) was synthesized according to the method described in Example 2 above. The conjugation of HYA with the copolymer was performed as described in Example 3 above. The condensation of polymer with HYA was carried out using the polymer/protein ratio 5:1 at pH=8. The final preparation of conjugate contained 0.15 mg of HYA per 1 mg of conjugate.

Example 5

Conjugation of Hyaluronidase (HYA) to SYNPOL 1000-20/50 Using the Activated Ethers Method A copolymer of ethylenepiperazine N-oxide and N-acetylethylenepiperazinium bromide (n=1000; q=0.2n; z=0.5) was synthesized according to Example 1 above. A two-step chemical procedure was used in order to get the covalent conjugate of HYA with the copolymer.

(1) In the first step, a succinimide ether of the copolymer was prepared. For this purpose, 100 mg of the copolymer were suspended in 4 ml of dimethylformamide and during stirring, 77.2 mg (0.30 mmol) of dicyclohexidcarbodiimide and 36 mg (0.30 mmol) of N-hydroxysuccinimide were added. The reaction lasted 24 hours during which the reaction mixture was stirred and cooled (2°–4° C.). The reaction mixture was the washed with dioxane, ethyl ether and acetone several times and dried in vacuum drier-box. The absence of low molecular admixtures was shown by thin-layer chromatography on "Silufol" plates in n-butanol:water:acetic acid (4:1:1). Then the content of activated ether groups was estimated by the standard method (T. Miron and M. Wilchek, Anal. Biochem.. 1982, v. 126, N2, pp. 433–435) (0.1M $NH_3$ water solution at pH=8.5, 259 nm, extinction coefficient=9700 1/mol×cm). The molar extinction coefficient "epsilon" was calculated from the Lambert-Beer equation:

$$D = \text{epsilon} \times C \times L,$$

where:
- D—the value of optical density;
- C—the concentration of the compound in the solution examined; and
- L—the optical path.

The content of activated ether group was $9 \times 10^{-4}$ mol per 1 g of the modified copolymer.

(2) In the second step of the procedure, the covalent coupling of HYA to the above succinimide ether of the copolymer was carried out. For this purpose, 100 mg of the activated copolymer produced in step (1) above were dissolved in 10 ml of 0.05M phosphate buffer solution (pH 6.0), cooled, and during continual stirring, a solution of 15 mg HYA dissolved in 12 ml of 0.05M phosphate buffer (pH 7.5) was added. The reaction of condensation lasted 18 hours at 0° C. Then the conjugate was isolated from the reaction mixture by column chromatography on the Biogel P-100 (BioRad) column and analyzed as described in Example 3 above. The final preparation of the protein-polymer conjugate contained 0.10 mg of HYA per 1 mg of conjugate.

Example 6

Preparation of the Covalent Conjugate of HYA to SYNPOL with a 2:1 Ratio in the Conjugate SYNPOL 1000-20/50 was synthesized according to the method described in Example 1 above. The conjugation of HYA with synpol was performed as described in Example 3 above with only one change in the procedure protocol: the initial ratio of SYNPOL to HYA in the reaction mixture was 2:1. The final conjugate preparation contained 0.3 mg of HYA per 1 mg.

Example 7

Vaccine Preparation

The vaccine prepared consisted of the HYA-SYNPOL conjugate and an additional amount of SYNPOL itself acting as an immunoadjuvant.

SYNPOL 1000-20/50 was obtained as in Example 1. The conjugation of HYA with Synpol was carried out as in Example 3 using the initial polymer/protein ratio 1:1. Namely, 5 mg of HYA was conjugated using the hydrazide method with 5 mg of SYNPOL 1000-20/50. Then the water solution of 40 mg of Synpol 1000-20/50 was added to the purified conjugate, mixed and lyophilized. The HYA content in the final complex preparation was analyzed as in Example 3 and showed 0.1 mg of HYA per 1 mg of the preparation.

Example 8

Vaccine Complex Containing the Derivative of Muramyldipeptide as the Immunoadjuvant The vaccine complex prepared was composed of both the HYA-Synpol conjugate and the glycosaminyl derivative of muramyldipeptide, a known immunoadjuvant.

SYNPOL 1000-20/50 was synthesized as in the Example 1. The covalent conjugate of HYA with Synpol was obtained as in Example 3 using the polymer/protein ratio 1:1. Namely, 5 mg of HYA was conjugated with 5 mg of SYNPOL 1000-20/50. then 10 mg of N-acetylglucosaminyl-N'-acetyl-muramyl-L-alanyl-D-isoglutamine (GMDP) was added and the complex mixture lyophilized.

Example 9

Vaccine Complex Containing Aluminium Hydroxide as an Immunoadjuvant

The vaccine complex consisted of HYA-SYNPOL conjugate and aluminium hydroxide as an immunoadjuvant.

SYNPOL 1000-20/50 was obtained as in Example 1. The polymer/protein ratio 1:1 was used during the covalent conjugation of SYNPOL with HYA using the method described in Example 3. The conjugate preparation was thoroughly mixed with a suspension of aluminium hydroxide ex tempore, just prior to immunization of animals.

Example 10

Preclinical Safety Evaluation of H-Polyvac

H-Polyvac is a polymer-antigen vaccine against migratory forms of helminths. The vaccine is a conjugate of hyaluronidase, HYA, with the polymer immunostimulant SYNPOL. The protein antigen HYA is common for many forms of larval helminths. SYNPOL was developed and thoroughly investigated by the applicants. The polymer was shown to be safe for the human organism in a dose of 0.25 mg/kg and therefore may be recommended both as a stand-alone immunostimulant and as an adjuvant and/or carrier for vaccines. The Committee on Immunobiological Drugs has given permission for the injection of SYNPOL as a compound of conjugate vaccines. The recommended dose for agricultural animals (sheep, calf) of H-Polyvac is 4 mg/animal, containing 0.5 mg of HYA antigen.

The purpose of this study was a toxicological assessment of the H-Polyvac vaccine to evaluate its safety. In order to increase the reliability of the data obtained the study was carried out on 3 species of animals (mice, rats and guinea pigs). Not only the influence of doses close to the vaccination dose was investigated, but in addition the effects of overdosing were investigated with doses 10–100 times higher than the vaccination dose. The usage of high doses in a toxicological study permits one to establish the target organs as well as to obtain the toxicological characteristics of the preparation used. Pathological changes, which are detected during injection of high doses, are not considered to be contraindications for clinical trials, but give valuable information concerning the limitations of the tested preparation.

Before presenting the actual details of the trials and the data obtained, the following remarks are helpful when interpreting the results. As can be seen in Table 8 below, pneumonia, lung atelectases and lung abscesses occurred in 10–20% of rats in the control placebo group. It is a well known fact among experts in animal pathology, that most rats, mice and other laboratory animals kept in conditions standard in the animal-breeding facilities of large laboratories are not completely healthy. They in fact suffer from various pathologies, which usually cannot be established without pathomorphological examination of their inner tissues and organs.

For example, latent infections of a bacterial etiology have been carefully investigated in laboratory animals (K. Benirschke, editor, Pathology of Laboratory Animals, N.Y. 1978). The frequency of lung diseases in control (clinically healthy) rats is rather high. According to G. Paget and P. Lemon more than 99% of control laboratory rats have a latent pathology in their lungs (Pathology of Laboratory Animals. Eds. W. Ribelin and J. McCoy, Springfield, 1965, pp. 382–405). Similarly, J. Nelson has shown 81% frequency of pneumonia in control laboratory rats (Pathology of Laboratory Rats and Mice. Eds. E. Cotchin and F. Roe. Oxford, 1967. p. 259). The pathomorphology of the so-called "latent chronic respiratory disease" in laboratory rats has been described by J. Innes et al (Am.J.Path., 1956, v.32, pp. 141–160; and in Pathology of Laboratory Rats and Mice. Eds. E. Cotchin and F. Roe, Oxford, 1967, pp. 229–259) as well as by J. Lindsey et al. (Disease of Laboratory Animals Complicating Biomedical Research, Chicago, 1971, pp. 675–716).

According to J. Lindsey (op.cit), E. Venzon et al. (Philipp.J.Vet.Med., 1979, v.18, pp. 117–124), and M. Van Zwieten et al. (Lab.Anim.Sci., 1980, v.30, pp. 215–221) the hidden pathological processes in lungs of rats are mainly induced by *Mycoplasma pneumoniae, Pasteurella spiralis* and/or mouse pneumonia virus.

Extensive examination of clinically normal WAG, August and Wistar inbred rats, and of noninbred animals of the production colonies of the Russian Academy of Medical Sciences, showed that 40–96% of rats were affected with chronic respiratory diseases. The respiratory organs were partially or totally involved in chronic catarrhal or catarrhal-purulent inflammation of the upper respiratory tract, trachea, bronchi, as well as in the development of chronic focal interstitial pneumonia (E. Abdrashitova, Respiratory organs of rats bred in the production colonies, Bull.Acad.Med.Sci.Russ., 1993, N9, 81–85). Concerning chronic enteritis, we note that its precise etiology has not been established, but it is likely they are symptoms of hidden infectious diseases. Most likely in these cases it was a clinically hidden chronic inflammation induced by certain kinds of bacteria as above.

It is thus clear that so called "normal" animals often suffer from hidden infections. It is a widely accepted opinion that this occurs because of non-optimal living conditions, commonly found in most vivariums. While this situation is not optimal as regards research work and animal trials of compounds, there are, however, some positive conclusions concerning the control animals in the trials: since the animals used were weakened because of "hidden" infections, the trial results show the complete safety of H-Polyvac (10× doses injected 10-times) not only for healthy animals, but even for weakened ones. Finally, it may be added that the trial results obtained on normally-infected laboratory animals are significantly closer to those obtained in real farm conditions.

1. Materials and Methods of the Study

The program of preclinical safety evaluation of H-Polyvac included an evaluation of acute toxicity in mice during intraperitoneal infusion, and of chronic toxicity during daily H-Polyvac injections continued for ten days in doses 10× higher than the vaccination dose; this was accompanied by peripheral blood analysis, liver and renal functional tests, examination of the cardiovascular system and pathomorphological analysis of changes in internal organs. In addition, investigations of local reactions to the injections as well as allergic, mutagenic, pyrogenetic and carcinogenic effects were carried out.

A dose of 4 mg (0.5 mg of protein for the sheep with a weight of 10–15 kg) was taken as 1 dose of the vaccine.

2. H-Polyvac Acute and Subacute Toxicity Evaluation

The average lethal dose of H-Polyvac was established in acute experiment on mice with a baseline weight of 25 g. The animals were carefully selected according to their body weight, each varying from the baseline weight by less than 1 g., i.e. by less than 5%. Each dose was tested on 6 animals with a period of observation of 16 days; mortality checks were performed daily.

At the end of the 2 weeks of observation, the animals were killed and their organs examined morphologically. After H-Polyvac samples were dissolved in a physiological solution, a 5% solution was prepared and then injected intraperitoneally in doses containing 3 g/kg, 1.5 g/kg and 0.75 g/kg of vaccine respectively.

The average lethal dose was determined using the probit-analysis technique under Litchfield and Wilcockson, which is the most widely applicable and allows one to obtain relatively complete information.

The data in Table 1 demonstrate that H-Polyvac LD-50 is 1.66+0.04 g/kg.

3. Assessment of the Local Response to H-Polyvac Injection

Intracutaneous injections. Experiments assessing the local reactions to H-Polyvac injections were performed according to techniques recommended by Directive No. 31 of USSR Ministry of Health, "Unification of Immunobiological Drug Control Techniques".

5 guinea pigs were used in this experiment; physiological solution and H-Polyvac (800 mg in 0.1 ml), diluted to 1:10 and 1:100 were injected once, intracutaneously, to different regions in a volume of 0.1 ml, after removing hair.

The observation period was 1 month.

Conclusion: there were no visible signs of skin inflammation during the period of observation.

4. H-Polyvac Subacute Toxicity Evaluation

The experiment was carried out on 60 male Wistar rats, with a baseline weight of 270–320 g. Animals were allocated to 3 groups, each group containing 20 rats. The first group of animals received 0.4 mg/kg of H-Polyvac, the second group received 4 mg/kg of H-Polyvac while the other third group acted as a control group and received physiological solution. H-Polyvac was injected intramuscularly each day for 10 days. Some animals were killed immediately after the termination of H-Polyvac administration, and the others 4 weeks after termination physiological, biochemical, hematological and histological tests were performed as well as regular body-weight evaluation. The results were then evaluated by statistical methods.

Figure 4:
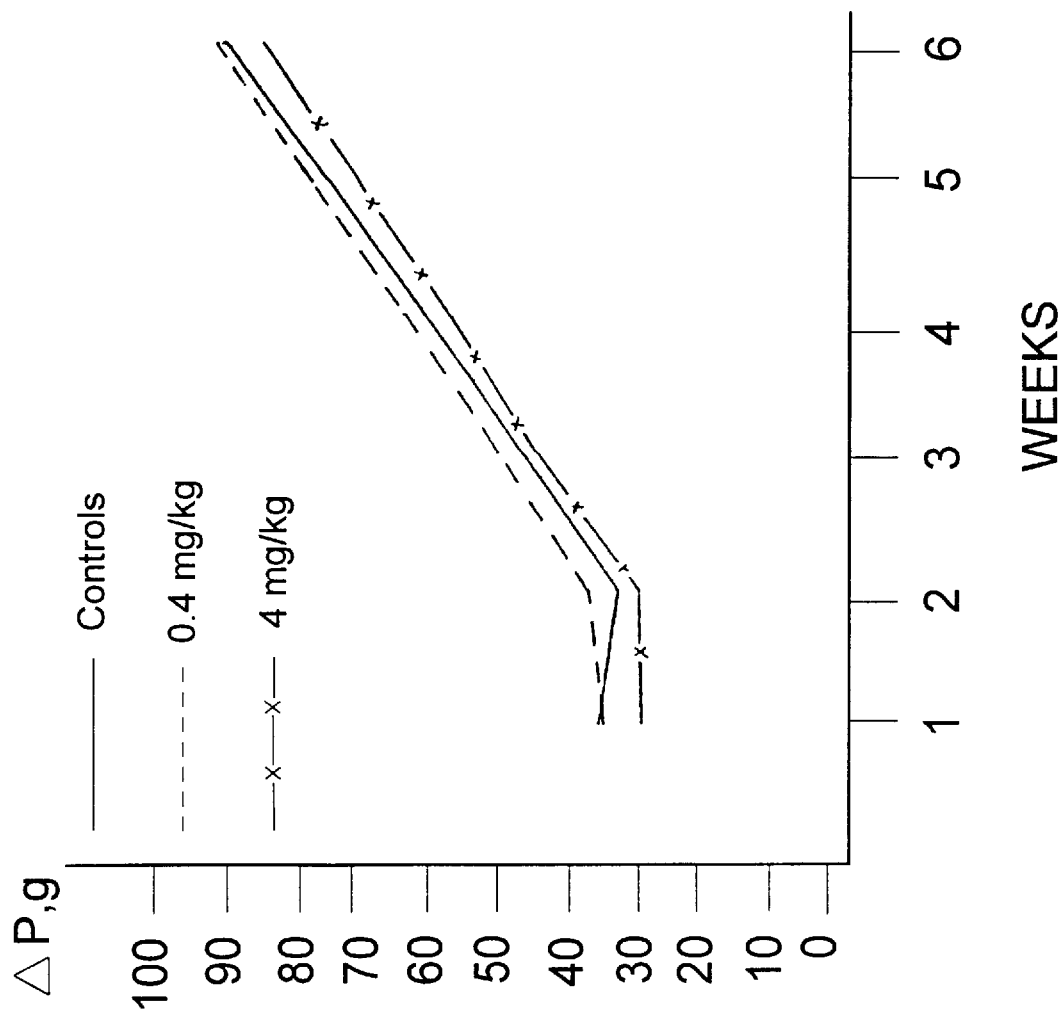
FIG. 4 is a graph indicating the changes in rat body weight after injection of a compound of the present invention.

Results: There was no significant difference in the body-weight gain of experimental animals as compared to the controls during the entire period of observation (6 weeks), at the same time body weight gain in animals, receiving 4 mg/kg is lower than in animals receiving 0.4 mg/kg (FIG. 4).

4.1 Liver and Renal Functional Tests

Blood serum analyses were performed using F-901 Biochemical Analyzer (Finland) and diagnostic kits LAHEMA (USSR). The results are presented in Table 2. The table shows that there was some increase in ALT activity after both 0.4 mg/kg doses and 4 mg/kg doses (14.5 and 19%, respectively). The biochemical range of blood serum of experimental animals did not differ from that of the controls 4 weeks after terminating the study.

Daily diuresis and diuretic speed were examined in order to evaluate renal function. In addition, glomerular filtration and channel reabsorption were tested. The results are presented in Tables 3 and 4. Analysis of the data obtained demonstrated that neither renal filter membrane-permeability, channel reabsorption nor glomerular filtration were affected by daily injections of H-Polyvac for 2 weeks.

4.2 Hematological Analysis

The red blood cell count and total leukocyte count using Goryaev Chamber as well as the haemoglobin concentration, hematocrit ratio, color index and corpuscular haemoglobin concentration, were measured in order to evaluate the status of peripheral blood. The color index was determined as:

$$\frac{Hb(g/1) * 3}{Eryth. (10/1)}$$

Corpuscular haemoglobin concentration was determined as:

$$\frac{Hb(g/1) * 3}{Ht(1/1)} * 10 = \%$$

where Ht=hematocrit and HB=haemoglobin.

The results are presented in Table 5.

The data demonstrate, that the hematocrit ratio decreases significantly only in the group receiving the 10-fold dose of 4 mg/kg as compared to control group. This decrease does not exceed normal physiological variations of that parameter in rats. There were no other significant abnormalities in the peripheral blood, both immediately after 10 H-Polyvac injections and one month after terminating the administration.

4.3 Central Nervous System (CNS) Status Examination

The experiments were performed on male Wistar rats. H-Polyvac was injected intramuscularly each day for 10 days, while the control group received physiological solution. The evaluation of H-Polyvac's influence on the functional state of the CNS was carried out the day after final injection and then repeated one month later.

The following tests were performed:

orientation reactions and locomotion activity which are integrative parameters reflecting CNS status and neuromuscular activity;

"Hole" reflex, which also characterizes orientation reactions;

spinal cord "tail flick" reflex, which characterizes animal pain perception;

"string"-test, which characterizes muscle tone and movement coordination.

These tests constitute a complete examination of the CNS status. (Methodical recommendations in use of behavioral reactions of animals in toxicology studies, Kiev, 1980.)

The results are shown in Table 6 and 7. A decrease in locomotion activity (races) occurs in both groups, after termination of administration, while in the group receiving 0.4 mg/kg the difference from control is statistically significant ($p<0.05$). Locomotion activity is similar to control after the convalescence period. There were no significant differences in other tests as compared to the control animals.

4.4. Pathomorphological Analysis

Pathomorphological analyses were performed on male Wistar rats. H-Polyvac was administered intramuscularly, in 10 injections, each one of which contained 0.4 mg/kg and 4 mg/kg respectively. Physiological solution was used as a control. Study material was taken twice: directly after the termination of H-Polyvac injections (first series, 26 animals), and one month after final administration (second series, convalescence period, 25 rats). All animals were sacrificed by decapitation.

Necropsy was carried out after blood collection for biochemistry analysis, then a macroscopic examination of internal organs, serosa, and cavities was performed as well as measurements of organ weights, color, bloodfilling level, hemodynamic disturbances or other abnormalities.

For histological analysis the following organs, organ and tissue samples were taken from 36 animals (6 rats in each group): liver, kidneys, heart, lungs, testes, adrenal, thymus, spleen, lymph nodes of different localization, brain, spinal cord, stomach, intestine, colon, pancreas, thyroids, pituitary, subcutaneous cellular fat, and muscles in the place of injection. Whole organs and samples of organs and tissues were fixed in 10% formaldehyde saline, washed, treated with ethanol and placed in paraffin. At least 2 sections were placed on pieces of glass and stained with hematoxylin-eosin.

Pathological and reactive changes were frequently observed in the control animals' organs because of the dramatic spread of infections and parasite diseases (see above); hence, the frequency of abnormalities detected in each group.

4.4.2. Results of Macroscopic Examination

Changes observed during external examination and necropsy in animals, killed directly after the termination of H-Polyvac administration and 4 weeks later are presented in Tables 8 and 9. Both color and bloodfilling levels of the experimental subject killed directly after the termination of H-Polyvac administration and also those killed 4 weeks later were the same as control parameters. Table 10 displays the parameters of absolute internal weights in rats of the first and second series of experiments. There was a nonsignificant decrease of spleen weight in the first series group receiving 0.4 mg/kg, while a nonsignificant increase of groin lymph node weight occurred in a group receiving 4 mg/kg of H-Polyvac. The relative index of the weight of inner organs of animals sacrificed directly after the termination of H-Polyvac administration as well as of those killed 4 weeks later were similar to those of the control animals (Table 11). The expression "Relative index of the weight of inner organs" as used in this section, refers it is referring to the average of the ratio for each animal of the weight of the particular inner organ divided by the body weight and multiplied by 100%.

Macroscopic examination of the place of H-Polyvac injection (subcutaneous cellular fat, muscle) did not show any hemodynamic disturbances in animals killed directly after the termination of H-Polyvac administration (first series). Only 1 out of 9 control animals and one out of 8 in the group receiving 0.4 mg/kg had puncture hemorrhages in subcutaneous cellular fat. In the second series (convalescence period) puncture hemorrhages in subcutaneous cellular fat were observed in one rat out of 8 control animals. There were no signs of inflammation (redness, infiltrates) in all groups of the two series.

4.4.3. Results of Microscopic Examination

Place of injection.

There were no abnormalities in the microcirculation system found during histopathological examination of subcutaneous cellular tissue and hip muscle in rats of the first series (control, 0.4 gm/kg and 4 mg/kg). There was no edema, subcutaneous infiltration and productive reaction in either experimental or control groups.

Neither necrobiotic nor dystrophic changes in muscle fibers were observed in experimental and control animals.

There were no signs of inflammation in muscle tissue of control rats. At the same time, moderate mononuclear infiltrates were observed in 3 rats out of 6, receiving H-Polyvac in a dose of 0.4 mg/kg, with a prevalence of monocytes and macrophages. There was an increase both in the number and size of mononuclear infiltrates in 4 rats out of 6, receiving 4 mg/kg of H-Polyvac. Cells were also subjected to changes, with a prevalence of lymphocytes and frequent detection of plasma cells.

Small mononuclear infiltrates were observed only in one animal from the control group, and in one rat from the group receiving 0.4 mg/kg of H-Polyvac, 4 weeks after the termination of H-Polyvac administration during histological examinations of the injection sites; small mononuclear infiltrates were observed in muscle tissue. There were no microcirculation abnormalities, dystrophic or necrobiotic changes.

Internal organs

Termination of H-Polyvac injection.

Heart

Multiple small perivascular hemorrhages were observed in the myocardium of one out of 6 control rats and in one out of 6 receiving 0.4 mg/kg of H-Polyvac. There were no other changes in the microcirculation system in either experimental or control groups.

There was no edema or interstitial swelling, nor was there any inflammatory infiltration or stromal myocardial productive action. No discoid disintegration of myofibrils or myocytolysis was observed.

Hyperemia of vessels and capillaries, sometimes with hemorrhages was observed in the lungs of all groups. Atelectases (partial contracture of alveoli wall) as well as small focal emphysema was detected in some of the animals of both experimental and control groups. Poly- and mononuclear infiltrates were observed in the intersticies of both groups. Moderate activity of bronchus-associated lymphoid tissue was detected. H-Polyvac did not cause an increase in congestion events in the microcirculation system in doses of 0.4 mg/kg or 4 mg/kg, nor were there any signs of dystrophic, necrobiotic or inflammatory processes.

There were no changes in the microcirculation system, no dystrophic or necrobiotic changes in glomerulae and tubules of nephrons, nor were there signs of inflammatory reactions to doses of 0.4 mg/kg or 4 mg/kg.

There were no abnormalities in the liver microcirculation system in any groups. The structure of experimental and control organs was similar. No dystrophic changes in hepatocytes were found. One control rat had a small necrotic focus, while there were no necrobiotic signs in either experimental or control groups. Inflammatory changes (proliferation and hypertrophy of reticuloendothelial cells, poly- and mononuclear infiltrates) did not occur in any test groups.

There were no changes in the microcirculation system of the pancreas in all animals examined. Structural changes of the exocrine part (pancreatic acini) were not observed. There were no signs of dystrophic, necrobiotic and inflammatory processes after H-Polyvac injections in doses of 0.4 kg or 4 mg/kg.

Esophagus and stomach. There were no changes in the microcirculation system after H-Polyvac injections in doses of 0.4 mg/kg or 4 mg/kg. There were no signs of esophagus epithelium damage, nor of any epithelium damage in the cardiac, fundic or pyloric stomach regions, neither were there any inflammatory reactions.

Signs of chronic enteritis together with thickening, deformation, and sometimes attachment of villi to each other were observed in the small intestine of all control animals. Epithelial dystrophy, and desquamation accompanied by villi stromal infiltration were found. Profound changes with crypt destruction occurred in several parts of the small intestine. The expression of chronic enteritis varied from mild to severely atrophic. There were no changes in groups receiving 0.4 mg/kg or 4 mg/kg doses of H-Polyvac in comparison with control groups.

Colon. There were no changes in the microcirculation system after H-Polyvac injections in doses of 0.4 mg/kg or 4 mg/kg, nor in control groups. Colon mucosae were found to be intact, smooth and without edema. There were no signs of villi and crypt epithelium damage, dystrophic changes or desquamation. Regenerative epithelial activity appeared to be high. There were no inflammatory infiltrates.

There were no changes in the thymic microcirculation system of control animals. One rat out of 6, receiving 0.4 mg/kg of H-Polyvac had a hemorrhage in the cortical zone of the thymus. A increase in the permeability of the vascular wall with further hemorrhages were registered in 3 rats out of 6 receiving 4 mg/kg of H-Polyvac. This group appeared to have signs of accidental thymus involution (reflected in a decrease of the cortical zone area and an increase of the connective tissue area). Inflammatory reactions were not found in any groups tested.

Spleen. There were no changes in the microcirculation system after H-Polyvac injections in doses of 0.4 mg/kg or 4 mg/kg, or in control groups. A moderate trend of white pulp area reduction, as well as a diminution of the germinal centers was noticed in experimental groups. Cytoarchitectonics of the white pulp (ratio of germinal centers, T-dependent and marginal areas) was not altered. The activity of functional zones in experimental groups did not differ from that of the control group: the number of immunoblasts and plasma cells remained constantly low, as did the mitotic figures and pyknosis. There were no signs of dystrophic, necrobiotic or inflammatory processes in either experimental or control groups.

Mesenteric and groin lymph nodes. There were no changes in the microcirculation system in either experimental or control groups, nor were there signs of dystrophic, necrobiotic and inflammatory processes. Parameters of activity of three types of immunity (T-, B- and macrophagal), evaluated according the three-rank system, were similar both in experimental and control groups and were within normal ranges.

Brain. There were no changes in the microcirculation system seen during histological examination of brain sections, either in the control groups or in those which received H-Polyvac injections in doses of 0.4 mg/kg or 4 mg/kg. There were no changes in the vessels of the ventricle or meninges. No structural changes of cortical or other brain neurons along with proliferative glial reactions were observed.

Spinal Cord. There were no changes in the microcirculation system after H-Polyvac injections in doses of 0.4 mg/kg or 4 mg/kg, or in control groups. No structural changes of anterior and posterior horns, glial cells, white matter tissue, or inflammatory reactions were found.

Pituitary. There were no changes in the microcirculation system either in experimental or control groups. Pituitary cytoarchitectonics (adenohypophysis, pars intermedia, neurohypophysis) in rats receiving H-Polyvac injections in doses of 0.4 mg/kg or 4 mg/kg, were similar to those of the control animals. All types of hormone producing cells were present in the adenohypophysis epithelium and there were no signs of dystrophic, necrobiotic or inflammatory reactions in all groups tested.

Thyroid. There were no changes in the system in all groups studied. Structural organization of the thyroid functional unit (follicles) in the experimental group did not differ from the control group. Follicles were equally filled with nonvacuolized colloid, while epimonoium cells had monolayer cubic structure. Thyrocytes and C-cells appeared to be without dystrophic signs, increased growth or necrosis. Inflammatory stromal reactions were not found either in controls or in rats receiving H-Polyvac injections in doses of 0.4 mg/kg or 4 mg/kg.

Adrenal. There were no changes in the microcirculation system after H-Polyvac injections in doses of 0.4 mg/kg or 4 mg/kg, or in control groups. The ratio of functional areas (cortical and medulla zones) remained similar to control in both experimental groups. There were no signs of dystrophic or necrobiotic changes in secretory cells or inflammatory reactions in all groups tested.

Testes. There were no changes in the microcirculation system either in experimental or control groups. Epididymal structure remained undamaged and there were no dystrophic or necrobiotic changes, no desquamation of spermatogenic epithelium, Sertoli cells, nor was there any aspermatogenesis in all groups studied. No pathological changes or interstitial inflammation occurred in Leydig cells.

Thus, pathomorphological analysis demonstrated that:
chronic intramuscular injection of H-Polyvac in doses of 0.4 mg/kg and 4 mg/kg does not produce dystrophic and necrobiotic changes in any organs examined;

there were nonsignificant abnormalities in the microcirculation system of the following organs: in the thymus of one rat (out of 6) receiving 0.4 mg/kg doses of H-Polyvac and in three rats (out of 6) receiving 4 mg/kg doses of H-Polyvac; in the heart of one control rat (out of 6) and one experimental rat (out of 6), receiving 0.4 mg/kg of H-Polyvac;

intramuscular injection of H-Polyvac did not affect the frequency and intensity of spontaneous enteritis;

there was a trend towards a decrease in the parenchymal working areas (areas of thymic cortical zone and splenic white pulp) of thymus and spleen in both experimental groups; however, it is difficult to interpret the results obtained because of the activation of the immune system as a result of the development of spontaneous chronic enteritis. Convalescence period.

There were no signs of microcirculation abnormalities, dystrophic or necrobiotic changes, nor inflammatory reactions in any organs (except in the small intestine as mentioned above) in all groups tested, during histological examinations performed 4 weeks after terminating the administration of H-Polyvac.

Atelectases and small-focal emphysema (in 2 rats out of 6) were observed in lungs of experimental and control groups.

Signs of spontaneous chronic enteritis were found in the small intestine of all examined groups. Epithelium dystrophy and desquamation as well as round cellular infiltration of villi stromae was found. The intensity of enteritis varied from mild to severe in all tested groups.

Signs of age involution were found in thymus of all groups (control, 0.4 mg/kg and 4 mg/kg), accompanied by very low cortical activity.

Moderate activity of splenic functional areas was found, combined with a low intensity of plasma cell reaction inside red pulp and with occasional extramedullar hemopoietic focuses.

Conclusions: The results of pathomorphological analysis, performed in animals receiving 10 intramuscular injections of H-Polyvac, demonstrate, that H-Polyvac does not produce any pathological changes in all tested organs in doses 0.4 mg/kg and 4 mg/kg.

5. Experimental Testing of H-Polyvac for Allergenicity

Previous experiments have demonstrated the absence of Synpol sensitization activity. The purpose of this experiment was to check H-Polyvac vaccine for allergenicity, as SYNPOL is here used in conjunction with a protein antigen.

The experiment was performed on 40 guinea pigs, divided into 4 groups: first—control group, second—protein antigen, third—SYNPOL, and fourth—H-Polyvac group, 4 subcutaneous injections 2 mg/kg 1 time a week.

Cutaneous drop tests were carried out with a 2% water protein and SYNPOL solution.

The technique of histamine provocation, designed by P. L. Zeltser and V. N. Drozdov in 1980, for assessment of allergenic effects of enzymatic hydrolytic preparations, was used in order to detect sensitization reactions. The technique involves intraperitoneal and intracutaneous injection of the tested antigen in combination with 0.03 gm/kg histamine, followed by anaphylactic reaction for 1.5–2 hours. According to the technique, histamine acts as a vascular adjuvant for more rapid and distinct reflection of weak allergens' sensitization characteristics. The quantitative ratio and functional status of different lymphocyte populations, in double rosette-formation and mitogen-stimulated rosette-formation (MSRF) reactions (Table 12) modified previously for guinea pigs examination (Dudintsava et al., 1982) were evaluated in 10 experimental and 30 control animals, in order to determine the influence of H-Polyvac on immune lymphocytes.

The results showed only primary irritative effects of the 2% protein antigen solution, reflected in the vessels' dilation and hyperemia, in the first minutes following the placement of H-Polyvac. There were no reactions showing development of immediate or delayed sensitization.

These experiments demonstrated that neither sensitization nor quantitative or functional abnormalities of lymphocytes would develop after treatment of human organism with polymer antigenic vaccine. Certain adverse effects on vessels, though, should be taken into consideration when establishing contraindications.

6. Assessment of H-Polyvac's Ability to Induce Dominant Lethal Mutations

The experiments were carried out, according to the "Recommendations on New Drug Mutagenic Properties Control", adopted by the then USSR Ministry of Health in 1981.

The experiments were continued for 5 weeks during both pre- and postmeiotic stages of spermatogenesis. H-Polyvac was injected intraperitoneally in doses of 0.6 mg/mouse and 30 mg/mouse and followed by the placement of three virginal females with the males treated with H-Polyvac. After 18 days female mice were subjected to necropsy and considered for the number of dead and alive.

Conclusions: H-Polyvac did not induce lethal mutations in embryonic cells of mice. At the same time 30 mg/mouse (1.5 g/kg) is close to LD-50, equal to 1.66+0.04 g/kg, and caused death of males the first day after administration.

7. Assessment of H-Polyvac for Carcinogenic Activity

The assessment of H-Polyvac carcinogenic activity was carried out according to the recommendations of "The Committee on Carcinogenic Substances".

The reason for the performance of this experiment was the fact that the polymeric compound SYNPOL was present in the vaccine.

The experiment was performed on two species of animals: 400 female Wistar rats with a 150–180 g baseline weight and 40 mice (C57BI/6), sensitive to tumor development.

0.5 ml of 0.1% H-Polyvac solution in physiological saline was injected intraperitoneally, 2 times a week, for 8 months, in 14–15 injection courses with two-week interval in between. The animals received 100 mg of a protein/kg as a whole dose. Physiological saline was administered intraperitoneally to the control animals. Observations were generally continued until the natural death of animals, while some rats (exhausted, ill, with tumors) were sacrificed, the size of the tumor was established and macroscopic pictures of inner organs taken following their fixation in 10% formaldehyde solution.

The experiment lasted 2 years and 1 month. Four rats with spontaneous tumors were found in the control group in different periods within nine months of the initiation of the experiment, while 3 were found in the experimental group.

The first tumors appeared 0.5 years later in experimental rats than in the control group. The speed and size of tumor development were also significantly lower in experimental rats. To emphasize H-Polyvac's carcinogenic activity, another series of experiment was performed in C57BI/6 mice, in order to evaluate the effect of H-Polyvac on Luis carcinoma development in lungs.

Mice were chosen carefully according to their body weights (16 g) and divided into 4 groups, 10 rats in each group. Epidermal Luis lung carcinoma was transferred to all animals, by the subcutaneous injection of 1:1 tumor solution with 199 medium, in a volume of 0.5 ml.

Group 1 was the control group, group 2 and 3 received H-Polyvac in dose of 5 mg/kg intraperitoneally and subcutaneously after 48 hours, while group 4 received 2.5 mg/kg of carrier subcutaneously, correspondingly to the quantity of carrier administered to mice in groups 2 and 3. The treatment continued each day for 5 days.

The weight of the animals and tumor size were determined, a week after tumor was transferred, i.e. at the end of the fifth day of H-Polyvac administration. The mice were killed, their body weight measured, and their tumors measured and separated and their weights determined. The results are presented in Table 14. The table demonstrates that both H-Polyvac and the carrier used alone cause a reduction in tumor development of 43–28% (by weight). The size and weight of tumors are significantly lower in all groups, as compared to the control group.

Presumably, the polymeric immunostimulator SYNPOL has antitumor activity. These properties are preserved and/or increased in the polymer-antigen conjugate (Table 14, columns 2, 4).

8. Conclusion

A complete preclinical safety evaluation study of H-Polyvac was carried out in the Laboratory of Drug-Diagnostic Forms of the Russian Ministry of Health.

H-Polyvac is a conjugate of a protein antigen with the polymeric immunostimulator Synpol. H-Polyvac is recommended as a vaccine against migrating forms of helminths in a dose of 0.05 mg of protein/kg of the animal's weight, that corresponds to a two-fold 0.4 mg/kg intramuscular injection of H-Polyvac.

The safety evaluation of H-Polyvac was performed according to the requirements of the Pharmacological Committee of the USSR Ministry of Health (Directive of 31.12.1983), as well as the requirements of "The Veterinary Pharmacological Committee" (1974).

The experiments were carried out in various species of animals: mice (CBA and C57BI/6 lines) 220 animals; Wistar rats, 180 animals; guinea pigs, 85 animals.

The results demonstrate that H-Polyvac is a practically nontoxic substance (class 5 of danger, according to SOST 12.1.07-76) with LD-50 being 1.66+0.4 g/kg, during intraperitoneal infusion.

Chronic toxicity was tested during multiserial daily injections of H-Polyvac, in vaccination (0.4 mg/kg) and 10-fold (4 mg/kg) doses.

According to hematological, physiological, biochemical, immunological analysis, there were no negative effects of H-Polyvac on animals' body weights, behavior, central nervous system, cardiovascular system, liver and renal function or blood.

No pathological changes in any internal organs and tissues, were determined by pathomorphological analysis.

The absence of irritative activity in the place of injection, as well as the absence of allergic, immunotoxic and mutagenic activities were also established.

No carcinogenic activity, during prolonged administration of H-Polyvac (8 months) and 2.2 year observation of animals was detected.

Therefore, the results of H-Polyvac safety evaluation study demonstrate the safety of H-Polyvac as well as a wide therapeutic ratio area (more than 400). A therapeutic dose of 4 mg/kg of H-Polyvac can be considered as absolutely safe.

Example 11

Experimental and Pasture Trials

To evaluate the effectiveness of the vaccine embodiment of the present invention, a series of experiments and pasture trials were conducted in the former USSR. The term "H-Polyvac" as used in this Examples section refers to the vaccine composition of the present invention.

1. Protection conferred by H-Polyvac against experimental challenge with *Echinococcus Granulosus*

1.1. Introduction

The life cycle of *Echinococcus granulosus* consists of successive stages, first in dogs and then in either sheep, pigs or human. Two different stage-specific forms of *E.granulosus* live as parasites in the species mentioned. A scolex tape-like form lives in the intestine of dogs; the last link of the tape, which contains about thousand eggs (oncospherae) of *E.granulosus*, separates from the helminth and is disseminated in the excrement of the host. Sheep, pigs or humans can be invaded orally by eggs of *E.granulosus*. The cysta (bladder) form of echinococci then causes damage to the liver and/or lungs of the above animal species or humans. In order to evaluate the effectiveness of the H-Polyvac vaccine against echinococcosis, both artificial challenges of animals by *E.granulosus* as well as spontaneous invasion were investigated. Dogs were artificially infected using protoscolices, whereas lambs and piglets were infected using oncospherae of *E.granulosus*.

1.2 Protection of dogs against an experimental challenge by *E.granulosus*.

Initially, one needs to determine whether there is a protective effect of H-Polyvac against *E.granulosus*, and estimate approximately the range of effective doses for dogs.

In the first experiment, that which involved 24 three-month old dogs, the range between 0.5 mg and 50 mg of H-Polyvac was investigated. Three separate groups containing 6 dogs each were injected twice using either 0.5 mg, 5 mg, or 50 mg of H-Polyvac intramuscularly. The booster immunization was made 21 days after the first one. The remaining 6 dogs of a placebo group received injections of 0.9% NaCl saline. Two weeks after the booster immunization each of the 24 dogs was infected orally by 16,000 protoscolices of *E.granulosus*. One month later all the dogs used were killed and dissected, and the number of *E.granulosus* helminths parasitizing the intestine obtained.

The results represented in Table 15 clearly suggest that preliminary immunization of dogs significantly increases their resistance to an invasion by *E.granulosus*. The number of echinococci found in the intestine of dogs immunized by H-Polyvac, was 15–120 times less than in that of the placebo control group. Moreover, the protection intensity obviously depended on the H-Polyvac dose. The range about 5 mg. of H-Polyvac seemed to be optimal for immunizing dogs by twicerepeated injections.

The goals of the next experiment were both a repetition of the measurement of the protective effects of H-Polyvac against echinococcosis, and an investigation of which H-polyvac doses near 5 mg are optimal. For these purposes, four separate groups of 3 dogs each, totalling 12 dogs, were used this time (Table 16). The group I dogs received 4 mg (i/m) of H-Polyvac twice with a 21 days interval between primary and secondary immunizations. The dogs of group II received 8 mg of H-Polyvac twice. The group III dogs were primed by 4 mg and then boosted by 8 mg of H-Polyvac. Dogs in the group IV received saline and served as a placebo control. Two weeks after the booster immunization, all the dogs used were infected artificially by oral administration of 5,000 protoscolices of *E.granulosus*. One month later, the animals were killed, dissected, and the resulting invasion intensity was established by counting the number of *E.granulosus* in the intestine.

The results obtained are presented in Table 16, and confirm the data of the previous experiment. They demonstrate firstly the high efficacy of H-Polyvac in protecting dogs from intensive invasion by *E.granulosus*, and secondly that the 5 to 10 mg dose of H-Polyvac is the optimal one for intramuscular immunization of dogs. In fact, the control dogs of the group IV which did not receive H-Polyvac, were heavily invaded, possessing about 2,000 echinococci in their intestine. On the contrary, the dogs of group I which were injected twice with 4 mg of H-Polyvac, possessed 100–300 times less echinococci. An increase of the H-Polyvac doses to 8 mg led to an enhancement of its efficacy in protecting against echinococci. In the intestine of dogs in groups II and III which were immunized by H-Polyvac using (8 mg+8 mg) or (4 mg+8 mg) schedules respectively, only a small number (from 0 to 3) of echinococci were found (Table 16).

1.3. H-Polyvac against experimental challenge of pigs by *E.granulosus*.

In total, 40 piglets, aged 1 month, were divided into 4 groups of 10 piglets in each. All the animals in groups I, II and III were injected twice with 5 mg of H-Polyvac. The booster injection was made 7 days (group I), 14 days (group II), or 21 days (group III) after the priming injection of H-Polyvac. The ten piglets of the group IV received saline instead of H-Polyvac. 20 days after the booster immunization, all the animals were artificially challenged by *E.granulosus* using doses of 10,000 oncospherae per os. Seven months later, the pigs were killed and the bladder form of echinococci in the liver were counted.

All the pigs of the placebo group IV underwent echinococci invasion. Large echinococci bladders of size 15–20 mm were found, and the number of helminths varied between 8 and 12 bubbles per liver (Table 17). On the contrary, no echinococci were found in most of the pigs which received H-Polyvac. Among the pigs of groups I, II and III, 70%, 90% and 80% of the animals respectively were absolutely free of echinococci. Furthermore, when helminths were found, their number varied between 1 to 4 echinococci bladders per liver. In addition, the helminth larvae found in the pigs immunized by H-Polyvac were very small in size (about 2–3 mm).

Undoubtedly, the data shown in Table 17 demonstrates that of the range of intervals between primary and secondary injections of H-Polyvac shown, the interval of 14–21 days for immunization of piglets is preferred.

The data obtained clearly shows the high efficacy of H-Polyvac regarding the prophylaxis of experimentally induced echinococcosis in pigs. In addition, the results mentioned above established both the dose and immunizing schedule for the effective vaccination of piglets by H-Polyvac.

1.4. Protection of sheep against an experimental challenge by *E.granulosus*.

Lambs aged 2–5 months were used in these investigations. Three separate experiments involving 12, 20 and 20 lambs respectivley were performed.

The initial experiment was designed to test two doses of H-Polyvac in sheep, namely 5 mg and 10 mg, that were found as the effective doses for dogs and piglets. 12 lambs, each 3–4 months old, were divided into 3 groups of 4 animals each (Table 18). The group I lambs were immunized using intramuscular injections by 5 mg H-Polyvac twice with a 21 day interval between priming and boosting injections. In the same manner, 10 mg of H-Polyvac was administered twice to group II. The remaining 4 lambs served as a placebo control: they received 0.9% NaCl saline.

Two weeks after the secondary immunization, all the lambs used were infected by *E.granulosus* by oral administration of 10,000 oncospherae. Four hundred days later, sheep of all three groups were killed, dissected, and the number of the bladder form of *E.granulosus* in their liver and lungs counted.

The results obtained are represented in Table 18, in which the intensive invasion of the sheep in the placebo group is clearly noticeable. A large number of hydatid cysts of *E.granulosus* (mean=88 per animal) were found in the inner organs of sheep in this group. The animals that were immunized by H-Polyvac possessed 8–15 times less echinococci in their inner organs. Furthermore, the size of the echinococci bladders found in the H-Polyvac immunized sheep, was 1–2.5 mm, in contrast to 4–9 mm of that in the nonimmunized control animals.

A subsequent similar experiment involved 20 lambs, 3 months old, divided into 3 groups. Eight lambs were immunized twice with the interval of 21 days by 5 mg H-Polyvac intramuscularly (i/m) (Table 19). The other group of 8 lambs were injected subcutaneously (s/c) with a 5 mg dose of H-Polyvac, twice with a 21 day interval. Finally, the remaining 4 lambs received 0.9% NaCl saline, serving as a placebo control. Two weeks after the booster immunization, all the animals were infected by 10,000 oncospherae of *E.granulosus*. Results of this experiment represented in Table 19 are very similar to those of the initial experiment (see Table 18).

In addition to the high efficacy of the immunization (performed by twice repeated injections of 5 mg of H-Polyvac) in protecting the lambs from experimental challenge by 10,000 oncospherae, the results of Table 19 show that both i/m and s/c modes of injection of H-Polyvac are acceptable for the vaccination procedure.

In the third conclusive experiment, 20 lambs, each 4.5 months old, were divided into 3 groups according to the protocol represented in Table 20. Two different lots of H-Polyvac were used for immunization. The group I of 8 lambs was immunized twice by 5 mg of the lot No. 1 of H-Polyvac. The group II of 8 lambs received 5 mg of the lot No. 2 of H-Polyvac. The remaining 4 lambs served as a placebo control. Later on, 2 weeks after the booster immunization, all 20 lambs were infected by *E.granulosus* by oral administration of 10,000 oncospherae.

On the 425th day after the challenge, all the animals were slaughtered and dissected, and the number of the helminths in their liver and lungs counted. Results obtained reaffirm the high efficacy of H-Polyvac in protecting sheep against experimental invasion by a large number of oncospherae of *E.granulosus* (Table 20). In fact, control sheep of the placebo group were heavily invaded carrying a large number (mean=65 helminths per animal) of echinococci in their liver and lungs. Both lot No. 1 and lot No. 2 of H-Polyvac, injected twice in a dose of 5 mg (i/m), strongly elevated the resistance of lambs to the challenge by *E.granulosus*. Some of those animals (3 out of 8 sheep in group I, i.e. 37.5%) were totally free from echinococci in their inner organs. The remaining immunized sheep carried a small number (mean values are 3 and 2.5 per animal in the groups I and II, respectively) of the echinococci bladders in their liver and lungs. Moreover, the helminth hydatid cysts found int he H-Polyvac immunized sheep were smaller in size (2–3 mm) than those found in the control animals (5–7 mm).

1.5. Conclusions concerning the efficacy of H-Polyvac in preventing experimental echinococcosis in dogs, pigs and sheep.

The investigations reviewed above in items 1.1–1.4 of H-Polyvac's activity in animals artificially infected using large doses of *E.granulosus* permit us to draw the following conclusions: (a) preliminary immunization of dogs, sheep, and pigs leads to a significant increase in their resistance to invasion by *E.granulosus*; (b) immunization by H-Polyvac defends the animal species mentioned even against a strong and intensive attack by echinococci, mimicked by an artificial acute challenge of animals with thousands of invasive helminths; (c) the protective effect of H-Polyvac against *E.granulosus* strictly depends on the H-Polyvac dose. Doses of 5–10 mg of H-Polyvac injected twice, intramuscularly or subcutaneously, with a 14–21 day interval between priming and boosting, were found to be optimal for immunizing either young dogs, 1 month old piglets, or 3–5 month old lambs.

2. Protection conferred by H-Polyvac against experimental challenge with *Dictyocaulus filaria*

For the hyaluronidase-antigen, included in H-Polyvac which is common for different species of helminths, one expects a protective action of H-Polyvac not only against echinococci, but also against other helminth species. This section is dedicated to the investigations made in order to estimate the protective effects of H-Polyvac in sheep as regards their resistance to an artificial challenge by a large number of *D.filaria*. This helminth infects animals as a invasive stage 3 larva (L3), entering an organism per os. The parasite then penetrates the intestine wall and migrates in the host, finally reaching its lungs. Here it grows for several weeks and develops into the mature stage. Growing within the lung tissue, the mature lungworms of 3–10 cm in size destroy their microenvironment in such a way as to result pneumonia, atelectases and abscesses in the lungs. Taking into consideration the life cycle of *D.filaria*, in the experimental challenge lambs were infected orally by 500 L3-larvae and then 2 or 3 months later the number of *D.filaria* in the lungs was counted.

In total, three separate experiments were performed using H-Polyvac in artificially induced dictyocaulasis. In the first experiment, 12 lambs, 3–4 months old, were used: four of them were injected twice with 5 mg H-Polyvac (lot No. 1) intramuscularly, while the other 4 lambs received the same dose of lot No. 2 H-Polyvac. The booster immunization was made 21 days after the primary one. The remaining four lambs served as a placebo control (Table 21).

Two weeks after the booster immunization the animals were artificially challenged using doses of 500 dictyocaulae larvae per os. Two months later, the animals were killed and the number of *D.filaria* per organism counted. The immunization of lambs by H-Polyvac made them resistant to the intensive acute invasion by *D.filaria* (oral administration of 500 larvae). Two months after the challenge, about 15% of the immunized animals were totally free from *D.filaria*. The remaining H-Polyvac immunized animals were invaded by a small number (mean about 4 or 5 helminths per body), whereas the nonimmunized animals in the corresponding control group underwent heavy dictyocaulae invasion (mean value=67 helminths per animal).

The following two experiments, summarized in the Table 22, produced very similar results to those of the Table 21. Briefly, the immunization of 2–3 month old lambs using 5 mg (i/m, twice with 21 day interval) H-Polyvac protected animals against intensive challenge by 500 larvae of *D.filaria*.

Thus, the protective influence of H-Polyvac is not restricted to *E.granulosus*. As was clearly shown in this section, H-Polyvac is also effective in the experimental model of an intensive invasion of lambs by *D.filaria*. The same H-Polyvac doses and immunization scheme were found to be effective in both helminthiases investigated.

3. Protection conferred by H-Polyvac against experimental challenge with *Fasciola hepatica*

Lambs 3–4 months old were used in the two experiments discussed below. The animals were immunized by H-Polyvac using 3–10 mg doses according to the protocols shown in Tables 23 and 24. Two weeks after the booster injection, the immunized, as well as control (placebo) animals, were invaded artificially by *F.hepatica*. For this purpose, the oral administration of 50 or 100 invasive larvae, named metacercaria, were used. Five to seven months later, the animals were killed and dissected, and the number of fasciolae in their livers were counted.

The results obtained demonstrate a significant protective influence of H-Polyvac. The twice-repeated injection of 3 or 5 mg of H-Polyvac led to a 50% decrease of the number of helminths surviving the host organism, even after an intensive challenge such as by oral administration of 100 metacercariae (see Table 23).

As soon as the challenge dose of metacercariae was halved, the protective effect of H-Polyvac reached 95–96% (see Table 24).

The experiments performed constitute clear evidence that H-Polyvac induces an immune defense against artificial invasion by a large number of fasciolae. Taken together with the data reviewed above in items 1 and 2, they show a polyspecific protective effect of H-Polyvac against three different helminth species, namely, *F.hepatica, D.filaria* and *E.granulosus*. Moreover, if the H-Polyvac immunization protects animals from an intensive acute challenge by large numbers of helminths used, one definitely expects a protective effect of the vaccine in animals which undergo spontaneous invasion by helminths under natural conditions. The pasture trials of H-Polyvac showed these expectations to be correct.

4. Polyspecific prophylaxis using H-Polyvac against spontaneous invasion by *E.granulosus, D.filaria* and *F.hepatica*

It is a well-known fact that certain helminth invasions are characteristic of animal farms and/or animal farming regions. Some localities (or farms) are unfavorable as regards dictyocaulasis, other as regards larval cestodae invasions, fascioliasis, and so on. The word "unfavorable" here means that from year to year each new generation of animals born in the farm/region undergoes the same invasion and the percentage of animals subject to invasion is very high (often more than 50%), and finally that the number of helminths of the particular species parasitizing the animal organism is sufficiently high as to lead to the manifestation of clinical symptoms of helminthiasis in the animals. Taking this into consideration, the pasture trials of H-Polyvac were performed in different animal farms and regions, unfavorable as regards echinococcosis, dictyocaulasis or fascioliasis. Sometimes invasion by multiple helminth species (of those mentioned) occurred during the trials.

4.1. Prevention of a spontaneous invasion of sheep and dog by *E.granulosus* under pasture condition.

The initial trials were performed at the USSR state sheep farm, named "Koyadinsky" of the Karaganda District (Central Kazakhstan) and at the collective sheep farm "Leninsky Poot" of the Chadyr-Langoon region (Moldova). Both farms are unfavorable as regards echinococcosis. In fact, more than 60% of sheep at these farms were normally invaded by echinococci.

According to the protocols shown in Tables 25 and 26, in total 75 2–3 month old lambs at the farm "Koyadinsky", as well as 135 lambs together with 11 shepherd's dogs at the farm "Leninsky Poot", were used. The animals were immunized twice by 5 or 10 mg of either Lot No. 1 or Lot No. 2 of H-Polyvac. They were kept separately from the flock they belonged to during the period of immunization of H-Polyvac and two weeks after the booster immunization. They then joined their flocks and lived under normal pasture conditions, being in touch with animals invaded by echinococci. One year later at the farm "Koyadinsky", and 8 months later at the farm "Leninsky Poot", the sheep were slaughtered and the numbers of echinococci in their livers and lungs counted. As can be seen at the Tables 25 and 26, the control nonimmunized sheep were heavily invaded by echinococci. On the contrary, those which had been immunized using H-Polyvac were significantly more resistant to the invasion. Under the protection of H-Polyvac the percentage of invaded animals decreased from 78% to 26%, and the mean number of echinococci per animal invaded diminished from 25 to 2 at the "Koyadinsky" or from 4.8 to 1.8 at the "Leninsky Poot". No significant differences between the protective effects of Lot No. 1 and Lot No. 2 of H-Polyvac were noticed.

In addition to echinococci the invasion by the relative cestodae of other species, namely, *Coenurus cerebralis* and *Cysticercus tenuicollis* was found in animals slaughtered at the farm "Leninsky Poot". Data presented in Table 26 showed that H-Polyvac immunization substantially elevated the resistance of sheep not only to invasion by echinococci, but also to invasion by *C.cerebralis* and *C.tenuicollis*.

The 11 shepherd's dogs were kept in pasture together with 135 sheep at the farm "Leninsky Poot". They were adult dogs and as they were already invaded by cestodae, they were treated by an antihelminthic named "Droncit" to get rid of their helminths before their immunization by H-Polyvac.

Subsequently they were injected twice with 10 mg of H-Polyvac (i/m, 21 day interval) and lived together with flocks which they controlled as usual. Every month the excrements of all 11 dogs were tested to estimate whether or not dogs were reinvaded by cestodae. Finally, 8 months after the H-Polyvac immunizations the dogs received antihelminthic to verify the invasion by cestodae. During the entire period of observation no cestodae were found in the dogs which had received H-Polyvac.

4.2. Protecting lambs from a spontaneous invasion of *D.filaria*.

These pasture trials were performed at the collective sheep farm "Druzhba" (Bolshenarymsky Region, Eastern Kazakhstan) and at the sheep farm "Maximoka" (Anneny Noy Region, Moldova), both unfavorable as regards dictyocaulasis. Usually 90–100% of sheep at the farms "Druzhba" and "Maximoka" are invaded by dictyocaulae. In total, 220 and 68 lambs, 1.5–2 months old, were used in trials at "Druzhba" and "Maximoka" respectively. The lambs were immunized by H-Polyvac and then two weeks after the booster immunization were sent to pasture and kept with the flocks to which they belonged. At the farm "Druzhba" the sheep were slaughtered 7 months after immunization, and the numbers of dictyocaulae in their lungs were ascertained (Table 27). The lambs involved in the trials at the farm "Maximoka" were not killed, but 5 months after the immunization by H-Polyvac the extent of *D.filaria* invasion was ascertained by coprological analysis of dictyocaulae larvae in their excrement (Table 28).

4.3. Prophylaxis of spontaneous invasion of sheep by *F.hepatica* under pasture conditions.

These trials were performed on the sheep farm "Poot Rybaka" (Dagestan, Russian Federation) and on the sheep farm attached to the Stavropol Station for Veterinary Research (Stavropol District, Russian Federation). In total, 243 and 50 lambs at the farms in Dagestan and Stavropol respectively were involved in the trials. Moreover, three different lots of H-Polyvac, namely Lots Nos. IG-4, IG-8 and IG-16, were used on three separate flocks of the sheep farm in Dagestan. Two lots of H-Polyvac (No. 1 and No. 2) were used within the same flock at the farm in Stavropol.

The lambs were immunized with H-Polyvac and 2 weeks later sent to join their flocks to live under normal pasture conditions. After 6, 7 or 10 months the lambs were slaughtered, and the number of fasciolae in their livers was calculated. Data, represented at Tables 29 and 30, show that H-Polyvac immunization significantly diminishes the susceptibiltiy of lambs to invasion by fasciolae.

All the lots of H-Polyvac used were efficacious in the prophylaxis of fascioliasis in lambs. It was useful to know that the combination of 5 mg H-Polyvac with 20 mg Synpol as an additional immunoadjuvant showed a slightly higher protective effect than 5 mg H-Polyvac itself. Later on this observation was confirmed and utilized during large scale trials of H-Polyvac (see item 5.2 below).

Thus, though the characteristics of the infection by acute artificial challenge using a large amount of invasive helminths (*E.granulosus, D.filaria, F.hepatica*) were significantly different in comparison with those of the spontaneous challenge under normal pasture conditions, both experimental and pasture trials of H-polyvac showed the same high efficacy of the preparation in the prophylaxis of the above-mentioned helminthiases.

5. State Trials of H-Polyvac

After reviewing the data of the experimental and pasture trials given above, the State Chief Directorate for Veterinary Medicine and State Veterinary Inspection of the former USSR decided to perform large scale trials of H-Polyvac under pasture conditions (order No. 46 of 11 May 1990). The state control trial-design pursued at least two goals: firstly, the verification of the efficacy of H-Polyvac on animal farms situated in different geographical and climatic regions of the country, and secondly, an estimation of the protective effect of H-Polyvac using large populations of animals.

5.1 The broad geography of the trials.

The list of sheep farms, unfavorable as regards echinococcosis, dictyocaulasis, or fascioliasis, included farms located in Ukraine (Kharkov and Soomy Regions, Crimea District), Moldova (Anneny Noy Reg. and Garakly Region), Georgia, Uzbekistan (Samarkand Region), Central, South and Eastern Kazakhstan, southern parts of the Russian Federation (Dagestan and Stavropol Districts), and central parts of the Russian Federation (Nyzhny Novgorod, Voronezh, Belgorod and Belaya Tserkov).

Table 31 summarizes the information about the localities and number of animals used during the State trials. The data from all the trials completely confirmed the initial results presented earlier. Briefly, it is convenient to summarize the results obtained using the efficacy coefficient (EC), that is:

$$EC = \frac{C - V}{C} \times 100\%$$

where C is the mean number of helminths per organism in the control group and V is the same parameter in the vaccinated group of animals having received H-Polyvac.

Using the efficacy coefficient, the data show H-Polyvac's effectiveness ranged between 82% and 90% in the prophylaxis of dictyocaulasis, and about 90% in the prophylaxis of fascioliasis, and finally was nearly 100% in the prevention of echinococcosis. As examples of the manner in which trials were conducted see below a brief discussion of the data from the trials involving thousands of sheep which were performed in Eastern Kazakhstan.

5.2. Trials of H-Polyvac on large populations of sheep under pasture conditions.

It is generally accepted opinion among experts in epidemiology and epizootiology, that the larger the population investigated is, the more precise the data obtained about the epidemiology of an infection. This is also true for estimating a new vaccine's effectiveness, and thus the data of H-Polyvac trials performed on thousands of lambs is of great value. Some examples are given below.

The protective properties of H-Polyvac were tested at the collective farm "Druzhba" (Eastern Kazakhstan) on 11000 lambs in pasture. The vaccine was administered twice in doses of 5 mg per animal to 20–30 day old lambs with an interval of 21 days, 45 days before the lambs were sent to pasture. A 20 year later when 1127 lambs were slaughtered 3–4 coenures per animal were found in 6 lambs, while no dictyocaulae, fasciolae, or echinococci were found. The percentage of invaded animals among unvaccinated sheep varied between 80% and 100% in different flocks on the farm.

The subsequent year H-Polyvac was tested at the same collective farm "Druzhba" on 11700 lambs in pasture. This time the vaccine was injected twice in a dose of 5 mg plus 20 mg of Synpol per animal into 20–30 day old lambs with an interval of 21 days, 45 days before they were sent to pasture. Seven months later, after the slaughter of 5000 lambs, 1–3 dictyocaulae were found in 25 lambs and no fasciolae or echinococci were found. The extensiveness of invasion in the control (unvaccinated) flocks was 90–100%.

Both examples of large scale trials of H-Polyvac clearly demonstrate its very high efficacy under real animal farming conditions.

TABLE 1

H-Polyvac Acute Toxicity Evaluation

| Dose of Vaccine g/kg | No of Alive | Dead/Alive | % Of Mortality |
|---|---|---|---|
| 3 | 6 | 5/1 | 83.1 |
| 1.5 | 6 | 3/3 | 50.0 |
| 0.75 | 6 | 0/6 | 0 |

TABLE 2

Biochemical Blood Serum Parameters of Male Rats During Intramuscular Injection of H-Polyvac

| Parameter | Units | Control | H-Polyvac 0.4 mg/kg | H-Polyvac 4 mg/kg |
|---|---|---|---|---|
| after 10 injections | | | | |
| Liver Mass quotient | | 4.15 ± 0.11 | 3.87 ± 0.10 | 3.85 ± 0.10 |
| Tot. Protein | g/l | 36.59 ± 0.56 | 36.34 ± 1.15 | 35.07 ± 1.04 |
| Glucose | mM/l | 8.90 ± 0.24 | 8.65 ± 7.28 | 9.28 ± 0.27 |
| Cholesterol | mM/l | 45.88 ± 3.37 | 78.90 ± 3.51 | 53.17 ± 4.05 |
| Urea | mM/l | 6.58 ± 0.32 | 6.44 ± 0.30 | 7.17 ± 0.27 |
| Creatinine | mcM/l | 74.4 ± 3.11 | 72.4 ± 4.37 | 77.9 ± 2.66 |
| Chlorides | mM/l | 101.5 ± 0.84 | 101.0 ± 0.72 | 102.2 ± 1.43 |
| ALT | U/l | 62.9 ± 3.65 | 72.0 ± 2.57* | 74.9 ± 3.97* |
| AST | U/l | 391.1 ± 41.87 | 386.5 ± 19.70 | 398.4 ± 32.21 |
| AP | U/l | 863.9 ± 71.62 | 825.3 ± 125.9 | 837.1 ± 70.38 |
| 4 weeks after terminating the administration | | | | |
| Liver Mass quotient | | 3.71 ± 0.18 | 3.74 ± 0.12 | 3.31 ± 0.09 |
| Tot. Protein | g/l | 38.70 ± 1.28 | 41.00 ± 0.76 | 41.62 ± 1.49 |
| Glucose | mM/l | 8.76 ± 3.20 | 8.16 ± 4.09 | 8.73 ± 3.57 |
| Cholesterol | mM/l | 54.15 ± 5.39 | 50.01 ± 3.21 | 46.49 ± 5.73 |
| Urea | mM/l | 7.36 ± 0.24 | 6.52 ± 0.36 | 6.90 ± 0.39 |
| Creatinine | mcM/l | 98.38 ± 3.13 | 91.33 ± 5.98 | 102.48 ± 4.78 |
| Chlorides | mM/l | 99.1 ± 0.26 | 100.0 ± 1.53 | 100.3 ± 0.83 |
| ALT | U/l | 75.8 ± 7.90 | 78.2 ± 6.08 | 69.4 ± 4.26 |
| AST | U/l | 343.7 ± 21.47 | 376.6 ± 28.51 | 355.9 ± 18.50 |
| AP | U/l | 491.0 ± 35.9 | 461.9 ± 33.4 | 518.3 ± 31.3 |

TABLE 3

Evaluation of Renal Function During H-Polyvac Injection

| Parameter | Substrate | Units | Control | H-Polyvac 0.4 mg/kg | H-Polyvac 4 mg/kg |
|---|---|---|---|---|---|
| Liver Mass Quotient | | | 0.67 ± 0.02 | 0.70 ± 0.02 | 0.66 ± 0.01 |
| Diuresis | | ml | 9.26 ± 0.72 | 9.10 ± 0.71 | 8.60 ± 0.72 |
| Diuretic Speed | | ml/mi | 0.0064 ± 0.0005 | 0.0063 ± 0.00049 | 0.006 ± 0.00049 |
| | serum | g/l | 36.59 ± 0.66 | 36.34 ± 1.15 | 35.07 ± 1.04 |
| Protein | urine | g/l | 6.16 ± 0.12 | 6.20 ± 0.24 | 6.80 ± 0.37 |
| | urine | g/24 h | 0.057 ± 0.004 | 0.056 ± 0.005 | 0.057 ± 0.003 |
| Urea | serum | mm/l | 6.58 ± 0.32 | 6.44 ± 0.30 | 7.17 ± 0.27 |
| | urine | mm/l | 893.7 ± 26.9 | 886.9 ± 77.6 | 941.0 ± 72.6 |
| | urine | mm/24 h | 8.19 ± 0.45 | 7.99 ± 0.75 | 7.97 ± 0.57 |
| | clear.* | ml/min | 0.87 ± 0.04 | 0.82 ± 0.05 | 0.78 ± 0.05 |
| Creatinine | serum | mcm/l | 74.4 ± 3.11 | 72.4 ± 4.37 | 77.9 ± 2.66 |
| | urine | mcm/l | 24025 ± 998 | 22782 ± 1399 | 23102 ± 1388 |
| | urine | mcm/24 | 219.7 ± 12.1 | 206.8 ± 21.7 | 194.6 ± 11.1 |

TABLE 3-continued

Evaluation of Renal Function During H-Polyvac Injection

| | | | | H-Polyvac | |
| --- | --- | --- | --- | --- | --- |
| Parameter | Substrate | Units | Control | 0.4 mg/kg | 4 mg/kg |
| | clear.* | ml/mi | 2.07 ± 0.18 | 1.92 ± 0.19 | 1.77 ± 0.11 |
| Chlorides | serum | mm/l | 101.5 ± 0.84 | 101.0 ± 0.72 | 102.2 ± 1.43 |
| | urine | mm/l | 51.6 ± 7.2 | 67.2 ± 8.16 | 65.0 ± 7.8 |
| | urine | mm/24 h | 0.54 ± 0.07 | 0.60 ± 0.07 | 0.55 ± 0.08 |

*clear. - clearance

TABLE 4

Evaluation of Renal Function 1 Month After H-Polyvac Injection

| | | | | H-Polyvac | |
| --- | --- | --- | --- | --- | --- |
| Parameter | Substrate | Units | Control | 0.4 mg/kg | 4 mg/kg |
| Liver Mass Quotient | | | 0.68 ± 0.02 | 0.69 ± 0.01 | 0.67 ± 0.03 |
| Dieresis | | ml | 11.3 ± 1.5 | 11.0 ± 0.6 | 10.9 ± 0.5 |
| Diuretic Speed | | ml/min | 0.0078 ± 0.001 | 0.0076 ± 0.0004 | 0.0076 ± 0.0005 |
| Protein | serum | g/l | 38.70 ± 1.28 | 41.00 ± 0.76 | 41.62 ± 1.49 |
| | urine | g/l | 5.48 ± 0.39 | 5.66 ± 0.28 | 5.30 ± 0.53 |
| | urine | g/24 h | 0.0062 ± 0.007 | 0.062 ± 0.003 | 0.057 ± 0.005 |
| Urea | serum | mm/l | 7.38 ± 0.24 | 6.52 ± 0.36 | 6.90 ± 0.39 |
| | urine | mm/l | 806.8 ± 49.9 | 852.0 ± 90.3 | 859.2 ± 64.8 |
| | urine | mm/24 h | 9.20 ± 1.05 | 9.40 ± 0.98 | 9.50 ± 0.73 |
| | clear.* | ml/min | 0.85 ± 0.09 | 0.96 ± 0.09 | 0.98 ± 0.10 |
| Creatinine | serum | mcm/l | 98.38 ± 3.13 | 91.33 ± 5.98 | 102.48 ± 4.78 |
| | urine | mcm/l | 21637 ± 217 | 23871 ± 241 | 20748 ± 139.5 |
| | urine | mcm/24 | 245.5 ± 20.6 | 259.5 ± 30.5 | 226.1 ± 22.9 |
| | clear.* | ml/mi | 1.70 ± 0.24 | 1.98 ± 0.22 | 1.59 ± 0.20 |
| Chlorides | serum | mm/l | 99.1 ± 0.26 | 100.0 ± 1.53 | 100.63 ± 0.83 |
| | urine | mm/l | 61.3 ± 8.3 | 53.8 ± 2.9 | 67.8 ± 4.12 |
| | urine | mm/24 h | 0.68 ± 0.08 | 0.60 ± 0.03 | 0.75 ± 0.073 |

*clear. - clearance

TABLE 5

Peripheral Blood Analysis in Male Rats After 10 Days of Intramuscular Injections of H-Polyvac

| | | | H-Polyvac | | |
| --- | --- | --- | --- | --- | --- |
| Parameter | Units | Control | 0.4 mg/kg | 4 mg/kg | |
| Leukocytes | 10/l | 13.75 ± 0.94 | 12.19 ± 0.99 | 12.84 ± 1.22 | |
| | | (11.7 ÷ 17.0) | (9.44 ÷ 15.6) | (9.0 ÷ 15.5) | |
| Erythrocytes | 10/l | 5.39 ± 0.57 | 4.84 ± 0.12 | 5.03 ± 0.14 | |
| | | (3.75 ÷ 7.00) | (4.60 ÷ 5.15) | (4.65 ÷ 5.50) | |
| Haematocrit Ratio | % | 47.56 ± 0.60 (45 ÷ 51) | 49.50 ± 1.07 (44 ÷ 53) | 44.67 ± 1.11 (40 ÷ 50) | ($p < 0.05$) |
| Haemoglobin | g/l | 204.3 ± 3.0 | 206.6 ± 2.4 | 198.6 ± 5.1 | |
| | | (186 ÷ 217) | (198 ÷ 217) | (166 ÷ 213) | |
| Colour Parameter | | 1.17 ± 0.12 (0.90 ÷ 1.58) | 1.27 ± 0.04 (1.18 ÷ 1.38) | 1.21 ± 0.04 (1.08 ÷ 1.30) | |
| Corpuscular Hb Concentration | % | 43.02 ± 0.87 (38.82 ÷ 46.30) | 41.87 ± 0.99 (38.65 ÷ 48.18) | 44.54 ± 1.06 (40.00 ÷ 48.50) | |

TABLE 6

CNS Functional Status Parameters in Male Rats after
10 Day Intramuscular Injections of H-Polyvac

| | | H-Polyvac | | |
| --- | --- | --- | --- | --- |
| Parameter | Control N = 9 | 0.4 mg/kg N = 8 | | 4 mg/kg N = 9 |
| Orientative-Explorative Behaviour (U) | | | | |
| Races | 72.8 ± 6.3 | 43.0 ± 8.0 | ($p < 0.01$) | 55.2 ± 7.5 |
| Sets | 25.2 ± 4.7 | 25.5 ± 7.5 | | 26.0 ± 7.9 |
| "Hole" - reflex | 3.1 ± 0.7 | 2.0 ± 0.5 | | 5.1 ± 0.8 |
| Pain Perception Threshold (c) | 6.76 ± 0.42 | 7.04 ± 0.42 | | 6.57 ± 0.23 |
| "String" - Test (mm) | 56.7 ± 3.0 | 54.4 ± 4.1 | | 51.1 ± 3.9 |

TABLE 7

CNS Functional Status Parameters in Male Rats One
Month of Reconvalescence after Intramuscular
Injections of H-Polyvac

| | | H-Polyvac | |
| --- | --- | --- | --- |
| Parameter | Control N = 9 | 0.4 mg/kg N = 8 | 4 mg/kg N = 9 |
| Orientative-Explorative Behaviour (U) | | | |
| Races | 40.6 ± 5.1 | 40.6 ± 8.4 | 33.9 ± 5.7 |
| Sets | 14.6 ± 4.2 | 28.4 ± 7.9 | 18.7 ± 6.4 |
| "Hole" - reflex | 3.7 ± 0.8 | 2.6 ± 0.6 | 3.6 ± 0.4 |
| Pain Perception Threshold (c) | 6.71 ± 0.40 | 6.23 ± 0.33 | 7.54 ± 0.27 |
| "String" - Test (mm) | 48.6 ± 3.5 | 44.1 ± 2.4 | 45.2 ± 2.8 |

TABLE 8

Frequency of Pathological Signs Observed in Animals,
Killed Directly after the Termination of the Drug
Administration

| | | H-Polyvac | |
| --- | --- | --- | --- |
| Changes | Control N = 9 | 0.4 mg/kg N = 8 | 4 mg/kg N = 9 |
| Pneumonia | 2 | 1 | 2 |
| Lung Lobe Athelectasis | 1 | 1 | 1 |
| Lung Abscess | 1 | 1 | 2 |
| Punctual haemorrhages in Thymus | 1 | 1 | 2 |
| Punctual Haemorrhages in Groin Lymph Node | 3 | 5 | 5 |
| Punctual Haemorrhages in Myocardium | 0 | 1 | 2 |
| Punctual Haemorrhages in the Place of Injection | 1 | 1 | 0 |
| Puncutal Haemorrhages in Liver | 1 | 0 | 0 |

TABLE 9

Frequency of the Pathological Changes During Necropsy
4 Weeks after Terminating the Administration of
H-Polyvac

| | | H-Polyvac | |
| --- | --- | --- | --- |
| Changes | Control N = 9 | 0.4 mg/kg N = 8 | 4 mg/kg N = 9 |
| Pneumonia | 1 | 1 | 2 |
| Punctual Haemorrhages in Lungs | 0 | 1 | 0 |
| Punctual Haemorrhages in Thymus | 1 | 2 | 2 |
| Punctual Haemorrhages in Groin Lymph Node | 3 | 2 | 2 |
| Punctual Haemorrhages in the place of Injection | 1 | 0 | 0 |

TABLE 10

Absolute Inner Organs Weight (in mg) of Animals,
Receiving H-Polyvac

| | Termination of administration | | |
| --- | --- | --- | --- |
| | | H-Polyvac | |
| Group Organs | Control N = 9 | 0.4 mg/kg N = 8 | 4 mg/kg N = 9 |
| Liver | 13.99 ± 0.49 | 12.70 ± 0.65 | 12.59 ± 0.53 |
| Kidneys | 2.25 ± 0.08 | 2.28 ± 0.07 | 2.16 ± 0.05 |
| Heart | 1.07 ± 0.04 | 1.07 ± 0.4 | 1.04 ± 0.03 |
| Lungs | 1.63 ± 0.05 | 1.57 ± 0.07 | 1.53 ± 0.04 |
| Thymus | 0.38 ± 0.04 | 0.35 ± 0.05 | 0.34 ± 0.03 |
| Spleen | 1.81 ± 0.09 | 1.53 ± 0.08* | 1.83 ± 0.09 |
| Adrenals | 0.06 ± 0.002 | 0.057 ± 0.002 | 0.056 ± 0.002 |
| Testes | 3.20 ± 0.09 | 3.45 ± 0.09 | 3.27 ± 0.10 |
| Groin Lymph Node | 0.08 ± 0.007 | 0.07 ± 0.006 | 0.09 ± 0.002 |
| Body weight (g) | 317.7 ± 11.2 | 327.4 ± 10.7 | 326.4 ± 7.9 |

TABLE 10-continued

Absolute Inner Organs Weight (in mg) of Animals,
Receiving H-Polyvac

| | | Convalescence Period | |
| --- | --- | --- | --- |
| | | H-Polyvac | |
| Group | Control | 0.4 mg/kg | 4 mg/kg |
| Organs | N = 8 | N = 8 | N = 9 |
| Liver | 13.69 ± 0.41 | 13.87 ± 0.48 | 12.00 ± 0.70 |
| Kidneys | 2.54 ± 0.06 | 2.57 ± 0.09 | 2.43 ± 0.08 |
| Heart | 1.15 ± 0.04 | 1.12 ± 0.04 | 1.17 ± 0.05 |
| Lungs | 1.64 ± 0.05 | 1.76 ± 0.08 | 1.67 ± 0.06 |
| Thymus | 0.25 ± 0.02 | 0.24 ± 0.02 | 0.24 ± 0.02 |
| Spleen | 1.27 ± 0.08 | 1.49 ± 0.09 | 1.48 ± 0.13 |
| Adrenals | 0.064 ± 0.002 | 0.064 ± 0.001 | 0.06 ± 0.001 |
| Testes | 3.38 ± 0.11 | 3.36 ± 0.12 | 3.44 ± 0.09 |
| Groin Lymph Node | 0.048 ± 0.006 | 0.063 ± 0.008 | 0.071 ± 0.03* |
| Body weight (g) | 370.3 ± 7.1 | 373.0 ± 15.4 | 367.8 ± 12.3 |

*Significant difference as compared to control ($p < 0.05$)

TABLE 11

Relative Internals Weight (in mg) of Animals,
Receiving H-Polyvac

| | | Termination of Administration | |
| --- | --- | --- | --- |
| | | H-Polyvac | |
| Group | Control | 0.4 mg/kg | 4 mg/kg |
| Organs | N = 9 | N = 8 | N = 9 |
| Liver | 4.16 ± 0.11 | 3.87 ± 0.09 | 3.85 ± 0.10 |
| Kidneys | 0.67 ± 0.01 | 0.70 ± 0.02 | 0.69 ± 0.02 |
| Heart | 0.32 ± 0.01 | 0.33 ± 0.01 | 0.32 ± 0.01 |
| Lungs | 0.48 ± 0.02 | 0.48 ± 0.02 | 0.47 ± 0.02 |
| Thymus | 0.11 ± 0.009 | 0.11 ± 0.01 | 0.11 ± 0.01 |
| Spleen | 0.54 ± 0.03 | 0.47 ± 0.02 | 0.56 ± 0.02 |
| Adrenals | 0.02 ± 0.0007 | 0.02 ± 0.0008 | 0.02 ± 0.0009 |
| Testes | 0.96 ± 0.04 | 1.06 ± 0.03 | 1.00 ± 0.03 |
| Groin Lymph Node | 0.02 ± 0.002 | 0.02 ± 0.002 | 0.03 ± 0.001 |
| Body weight (g) | 337.7 ± 11.2 | 327.4 ± 10.7 | 326.4 ± 7.9 |

| | | Convalescence Period | |
| --- | --- | --- | --- |
| | | H-Polyvac | |
| Group | Control | 0.4 mg/kg | 4 mg/kg |
| Organs | N = 8 | N = 8 | N = 9 |
| Liver | 3.72 ± 0.16 | 3.74 ± 0.11 | 3.31 ± 0.12 |
| Kidneys | 0.69 ± 0.02 | 0.69 ± 0.02 | 0.68 ± 0.03 |
| Heart | 0.31 ± 0.008 | 0.30 ± 0.11 | 0.33 ± 0.008 |
| Lungs | 0.44 ± 0.009 | 0.47 ± 0.02 | 0.46 ± 0.012 |
| Thymus | 0.07 ± 0.007 | 0.07 ± 0.006 | 0.07 ± 0.016 |
| Spleen | 0.34 ± 0.02 | 0.40 ± 0.02 | 0.42 ± 0.03 |
| Adrenals | 0.02 ± 0.0005 | 0.02 ± 0.0006 | 0.02 ± 0.0005 |
| Testes | 0.91 ± 0.02 | 0.91 ± 0.03 | 0.94 ± 0.03 |
| Groin Lymph Node | 0.011 ± 0.001 | 0.02 ± 0.002 | 0.02 ± 0.002 |
| Body weight (g) | 370.3 ± 7.1 | 373.0 ± 15.4 | 367.8 ± 12.4 |

*Significant difference as compared to control ($p < 0.05$)

TABLE 12

Quantitative Ratio and Functional State of Various Lymphocyte Populations after Treatment with H-Polyvac in Guinea Pigs

| Animal Groups Doses | No | Double Rosette-Forming Reaction No of lymphocytes | | | | MSRF-Reaction with Con A | |
|---|---|---|---|---|---|---|---|
| | | T | B | D | O | B | D |
| 1. 2 mg/kg of H-Polyvac | 10 | 49 ± 1.9 | 7 ± 0.9 | 5 ± 0.7 | 39 ± 2.4 | 1.0 ± 0.6 | 2.2 ± 0.3 |
| 2. Intact control | 6 | 47 ± 3.5 | 8 ± 1.2 | 5 ± 0.9 | 40 ± 4.6 | 0.9 ± 0.07 | 1.7 ± 0.1 |
| 3. 1 mg/kg of H-Polyvac | 8 | 56 ± 4.2 | 5 ± 0.9 | 4 ± 0.9 | 31 ± 2.5 | 0.9 ± 0.05 | 2.1 ± 0.3 |
| 4. Intact control | 6 | 41 ± 3.7 | 6 ± 1.4 | 4 ± 0.9 | 40 ± 4.6 | 1.1 ± 0.14 | 2.03 ± 0.3 |

TABLE 13

Registration of Dominant Mutations in Embryonic Cells of Mice

| Stage of Spermato-genesis | Substance Infused | No of Pregnant | Fertile % | Post-implant | Mortality Induced | Level of Mutagenic Effect | Mutager Activit Ratio |
|---|---|---|---|---|---|---|---|
| 1 week | H-Polyvac, 6 mg/mouse | 29 | 96.6 | 2.3 | 0 | 0 | 0 |
| | control | 28 | 93.3 | 2.0 | 0 | 0 | 0 |
| 2 week | H-Polyvac, 0.6 mg/mouse | 29 | 96.6 | 2.0 | 0 | 0 | 0 |
| | control | 29 | 96.6 | 4.0 | 0 | 0 | 0 |
| 3 week | H-Polyvac, 0.6 mg/mouse | 30 | 100.0 | 3.2 | 0 | 0 | 0 |
| | control | 28 | 93.3 | 4.2 | 0 | 0 | 0 |
| 4 week | H-Polyvac, 0.6 mg/mouse | 30 | 100.0 | 0.3 | 0 | 0 | 0 |
| | control | 30 | 100.0 | 2.4 | 0 | 0 | 0 |
| 5 week | H-Polyvac, 0.6 mg/mouse | 29 | 96.6 | 3.5 | 0 | 0 | 0 |
| | control | 29 | 96.6 | 0.2 | 0 | 0 | 0 |

Note: 10 males were used both in experiment and control.

TABLE 14

Influence of H-Polyvac and Polyoxidonium on the Development of Epidermal Luis Lungs Carcinoma in Mice C57BI/6

| Drug Dose (mg/kg) | Method of Infusion | Days of Observation | No Of Dead | Tumour Volume (mm) | % to Control | Tumour Weight (g) | % to Control |
|---|---|---|---|---|---|---|---|
| Control | s/c | 14 | 30% | 6080.25 | 100 | 3.23 | 100 |
| H-Polyvac, 5 mg/kg | s/c | 14 | 10% | 3621.75* | 59.6 | 1.85* | 57.0 |
| H-Polyvac, 5 mg/kg | i/p | 14 | 10% | 2869.82* | 47.2 | 2.33* | 72.2 |
| Polyoxidonium, 2.5 mg/kg | s/c | 14 | 10% | 3679.50* | 60.6 | 2.18* | 67.5 |

*$p < 0.014$

TABLE 15

| Animals | Immunization by H-Polyvac: Priming | Interval (days) | Boosting | Artificial Challenge by E. granulosus | Helminths in Intestine per Dog (mean) |
|---|---|---|---|---|---|
| 6 dogs | 0.5 mg i/m | 21 | 0.5 mg i/m | 16,000 protoscolices | 400 |
| 6 dogs | 5 mg i/m | 21 | 5 mg i/m | 16,000 protoscolices | 50 |
| 6 dogs | 50 mg i/m | 21 | 50 mg i/m | 16,000 protoscolices | 550 |
| 6 dogs | saline | 21 | saline | 16,000 protoscolices | 6,030 |

TABLE 16

| Group No. | Animals in Groups: Number | Age (mo.) | Immunizing Scheme by H-Polyvac: Priming | Interval (days) | Boosting | Helminths per Animal in 1 Mo. after Challenge by 5,000 protoscolices |
|---|---|---|---|---|---|---|
| I | 3 dogs | 3 | 4 mg (i/m) | 21 | 4 mg (i/m) | 8; 16; 12 |
| II | 3 dogs | 3 | 8 mg (i/m) | 21 | 8 mg (i/m) | 2; 0; 1 |
| III | 3 dogs | 3 | 4 mg (i/m) | 21 | 8 mg (i/m) | 3; 2; 2 |
| IV | 3 dogs | 3 | Saline | 21 | Saline | 2475; 2500; 1573 |

TABLE 17

| Group No. | Number of Animals | Immunization Scheme by H-Polyvac Priming | Intervals (days) | Boosting | Helminth hydatid cysts in Liver EI* | II** |
|---|---|---|---|---|---|---|
| I | 10 piglets | 5 mg | 7 | 5 mg | 30% | 3; 3; 4 |
| II | 10 piglets | 5 mg | 14 | 5 mg | 10% | 1 |
| III | 10 piglets | 5 mg | 21 | 5 mg | 20% | 1; 2 |
| IV | 10 piglets | Saline | 21 | Saline | 100% | 10; 10; 9; 12; 8; 12; 12; 11; 8; 9 |

*EI-extensiveness of invasion (percentage of invaded animals);
**II-intensity of invasion (number of helminths per animal).

TABLE 18

| Lambs in Group: Number | Age (mo.) | Immunization by H-Polyvac: Priming | Interval (days) | Boosting | Helminths in Liver & Lungs 400 days after Challenge Number of Echinococci per Animal | Approx. Size of hydatid cysts (mm) |
|---|---|---|---|---|---|---|
| 4 | 3–4 | 5 mg i/m | 21 | 5 mg i/m | 3; 6; 4; 11 (mean = 6) | 1–2.5 |
| 4 | 3–4 | 10 mg i/m | 21 | 10 mg i/m | 9; 13; 8; 12 (mean = 11) | 1–2.5 |
| 4 | 3–4 | Saline | 21 | Saline | 52; 78; 77; 146 (mean = 88) | 4–9 |

TABLE 19

| Lambs in Group: | | Immunization by H-Polyvac: | | | Helminths in Liver & Lungs: | |
|---|---|---|---|---|---|---|
| | | | | | Echinococci per | Size of hydatid |
| Number | Age (mo.) | Dose | Mode of Injection | Interval (days) | Animal (mean + SD) | cysts (mm) |
| 8 | 3 | 5 mg × 2 | i/m | 21 | 6 + 4 | 1–3 |
| 8 | 3 | 5 mg × 2 | s/c | 21 | 5 + 4 | 1–4 |
| 4 | 3 | Saline | s/c | 21 | 63 + 23 | 5–9 |

TABLE 20

Comparison of two different lots of H-Polyvac regarding their efficacy in protecting sheep from an experimental challenge by 10 000 oncospherae of *E. granulosus*.

| Sheep in Group: | | | Immunization by H-Polyvac: | | | Helminth Bladders in Liver and Lungs 425 days after challenge by *E. granulosus* | |
|---|---|---|---|---|---|---|---|
| Group No. | Number | Age (mo.) | Lot | Dose | Interval (days) | Number of Helminths per Animal | Approx. Size of hydatid cysts (mm) |
| I | 8 | 4.5 | Lot No. 1 | 5 mg × 2 i/m | 21 | 1; 0; 3; 8; 0; 0; 9; 4 (mean = 3) | 2–3 |
| II | 8 | 4.5 | Lot No. 2 | 5 mg × 2 i/m | 21 | 2; 2; 3; 2; 3; 2; 3; 3; (mean = 2.5) | 2–3 |
| III | 4 | 4.5 | | Saline i/m | 21 | 49; 64; 81; 65 (mean = 65) | 5–7 |

TABLE 21

| Lambs in Group: | | Immunization by H-Polyvac: | | Artificial Challenge by | Helminths in Lungs in 2 mo. after Challenge | |
|---|---|---|---|---|---|---|
| Number | Age (mo.) | Lot No. | Dose (i/m) | *D. filaria* (per os) | Number of Helminths per Animal (mean + SD) | Percentage of Animals Invaded by Dictyocaulae |
| 4 | 3–4 | Lot 1 | 5 mg × 2 | 500 larvae | 4 + 2 | 85% |
| 4 | 3–4 | Lot 2 | 5 mg × 2 | 500 larvae | 5 + 1 | 87% |
| 4 | 3–4 | Saline | 2 ml | 500 larvae | 67 + 9 | 100% |

TABLE 22

| Lambs in Group: | | | Immunization by H-Polyvac | | | *D. filaria* in Lungs in 1–2 Months after Challenge: | |
|---|---|---|---|---|---|---|---|
| Exp. No. | Number | Age (mo.) | Priming | Interval (days) | Boosting | Helminths per Animal (mean) | Percentage of Invaded Animals |
| 2 | 5 | 2.5–3 | Saline | 21 | Saline | 30 | 100% |
| | 18 | 2.5–3 | 5 mg i/m | 21 | 5 mg i/m | 4 | 89% |

TABLE 22-continued

| | Lambs in Group: | | Immunization by H-Polyvac | | | *D. filaria* in Lungs in 1–2 Months after Challenge: | |
|---|---|---|---|---|---|---|---|
| Exp. No. | Number | Age (mo.) | Priming | Interval (days) | Boosting | Helminths per Animal (mean) | Percentage of Invaded Animals |
| 3 | 10 | 2–3 | Saline | 21 | Saline | 32 | 100% |
|   | 10 | 2–3 | 5 mg i/m | 21 | 5 mg i/m | 1 | 60% |

TABLE 23

| Lambs in Group: | | Immunization by H-Polyvac: | | | Artificial Challenge by *F. hepatica* | Fasciolae per Liver 5 mo. after the Challenge (mean + SD) |
|---|---|---|---|---|---|---|
| Number | Age (mo.) | Priming | Interval (days) | Boosting | | |
| 4 | 3 | 3 mg | 21 | 3 mg | 100 metacercariae | 12 + 4 |
| 4 | 3 | 5 mg | 21 | 5 mg | 100 metacercariae | 10 + 3 |
| 4 | 3 | Saline | 21 | Saline | 100 metacercariae | 20 + 8 |

TABLE 24

| Lambs in Group: | | Immunization by H-Polyvac: | | | Artificial Challenge by *F. hepatica* | Fasciolae per Liver 7 mo. after Challenge |
|---|---|---|---|---|---|---|
| Number | Age (mo.) | Priming (i/m) | Interval (days) | Boosting (i/m) | | |
| 10 | 3–4 | 5 mg | 21 | 5 mg | 50 metacercariae | 1–3 |
| 10 | 3–4 | 10 mg | 21 | 10 mg | 50 metacercariae | 1–2 |
| 10 | 3–4 | Saline | 21 | Saline | 50 metacercariae | 28–37 |

TABLE 25

The pasture trials of H-Polyvac at the sheep farm "Koyadinsky"

| Lambs in Group: | | Immunization by H-Polyvac: | | | | Helminths in Liver & Lungs in 12 months after Immunization: | |
|---|---|---|---|---|---|---|---|
| Number | Age (mo.) | Lot | Priming (i/m) | Interval (days) | Boosting (i/m) | Number of Echinococci per Animal (mean + SD) | Approx. size (mm) |
| 25 | 2–3 | No. 1 | 5 mg | 21 | 5 mg | 3 + 2 | 3–4 |
| 25 | 2–3 | No. 2 | 5 mg | 21 | 5 mg | 2 + 1 | 2.5–3 |
| 25 | 2–3 | Saline | | 21 | Saline | 25 + 10 | 6–9 |

TABLE 26

The pasture trials of H-Polyvac at the sheep farm "Leninsky Poot"

| Lambs in Group: | | Immunization by H-Polyvac: | Cestodae in the Inner Organs in 8 Months after the Immunization: | | | | | |
|---|---|---|---|---|---|---|---|---|
| | | | *E. granulosus* | | *C. tenuicollis* | | *C. cerebralis* | |
| Number | Age (mo.) | (i/m) | EI* | II** | EI | II | EI | II |
| 45 | 2.5–3 | 10 mg × 2 | 26% | 1.8 | 13% | 2.5 | 0 | 0 |
| 45 | 2.5–3 | 5 mg × 2 | 40% | 3.1 | 46% | 1.5 | 7% | 1.0 |
| 45 | 2.5–3 | Saline | 78% | 4.8 | 89% | 4.0 | 11% | 1.0 |

*EI-extensiveness of invasion;
**II-intensity of invasion (see Table 3)

TABLE 27

The pasture trials of H-Polyvac at the sheep farm "Druzhba"

| Lambs in Group: | | Immunization by H-Polyvac | | | Helminths in Lungs in 7 mo. after the Immunization: | |
|---|---|---|---|---|---|---|
| | | | | | *D. filaria* | |
| Number | Age (mo.) | Priming (i/m) | Interval (days) | Boosting (i/m) | per Animal (mean + SD) | Percentage of Animals Invaded |
| 100 | 1.5–2 | 5 mg (lot 1) | 21 | 5 mg (lot 1) | 2 + 1 | 12% |
| 100 | 1.5–2 | 5 mg (lot 2) | 21 | 5 mg (lot 2) | 2 + 1 | 13% |
| 20 | 1.5–2 | Saline | 21 | Saline | 13 + 3 | 100% |

TABLE 28

The pasture trials of H-Polyvac at the sheep farm "Maximoka"

| Lambs in Group: | | Immunization by H-Polyvac: | | | Period in | Percentage of Animals |
|---|---|---|---|---|---|---|
| Number | Age (mo.) | Priming (s/c) | Interval (days) | Boosting (s/c) | Pasture (mo.) | Invaded by *D. filaria** |
| 28 | 1.5–2 | 5 mg | 21 | 5 mg | 6 | 25% |
| 25 | 1.5–2 | 5 mg | 21 | 10 mg | 6 | 16% |
| 15 | 1.5–2 | Saline | 21 | Saline | 6 | 100% |

*Coprology

TABLE 29

The pasture trials of H-Polyvac at the farm "Poot Rybaka"

| | Lambs in Group: | | Immunization by H-Polyvac | | Period in | *F. hepatica* per Liver |
|---|---|---|---|---|---|---|
| Flock | Number | Age (mo.) | Lot | Dose (i/m) | Pasture (mo.) | (mean + SD) |
| A | 40 | 2–3 | IG4 | 5 mg × 2 | 7 | 2 + 1 |
| | 40 | 2–3 | (IG4 + PO) | (5 mg + 20 mg) × 2 | 7 | 0 |
| | 20 | 2–3 | Saline | | 7 | 13 + 4 |
| B | 13 | 3 | IG-8 | 5 mg xp0 2 | 7 | 4 + 3 |
| | 10 | 3 | Saline | | 7 | 91 + 39 |
| C | 100 | 2–2.5 | IG-16 | 5 mg × 2 | 10 | 8 + 3 |
| | 20 | 2–2.5 | Saline | | 10 | 24 + 14 |

TABLE 30

The pasture trials of H-Polyvac at a sheep farm in Stavropol

| Lambs in Group: | | Immunization by H-Polyvac: | | | Period in | Number of |
|---|---|---|---|---|---|---|
| Number | Age (mo.) | Lot | Priming | Interval (days) | Boosting | Pasture (mo.) | F. hepatica per Liver |
| 20 | 2–3 | No 1 | 5 mg, i/m | 21 | 5 mg, i/m | 6 | 0 |
| 20 | 2–3 | No 2 | 5 mg, i/m | 21 | 5 mg, i/m | 6 | 0 |
| 10 | 2–3 | — | Saline | 21 | Saline | 6 | 7–32 |

| District | Animals Vaccinated by H-Polyvac | Helminthiasis Actual in the Region |
|---|---|---|
| Eastern Kazakhstan District | 580 lambs | Dictyocaulasis |
| Samarkand Reg., Uzbekistan | 600 lambs | Echinococcosis |
| Samarkand Reg., Uzbekistan | 80 piglets | Echinococcosis |
| Moldova | 1000 lambs | Echinococcosis |
| Belgorod Reg., Central Russ. Fed. | 70 lambs | Fascioliasis |
| Stavropol Reg, South Russ. Fed. | 500 lambs | Fascioliasis |
| Dagestan, South Russ. Fed. | 120 lambs | Fascioliasis |
| Nyzhny Novgorod Reg., Central Russ. Fed. | 50 lambs | Fascioliasis |
| Crimea Reg., Ukraine | 1000 lambs | Dictyocaulasis |
| Georgia | 50 lambs | Fascioliasis |
| Karaganda Reg., Central Kazakhstan | 75 lambs | Echinococcosis |
| Tseliograd Reg., Central Kazakhstan | 30 lambs | Dictyocaulasis |
| Dzhambul Reg., South Kazakhstan | 500 lambs | Echinococcosis |
| Kharkov Reg., Ukraine | 50 lambs | Dictyocaulasis |
| Soomy Reg., Ukraine | 100 lambs | Dictyocaulasis |
| Eastern Kazakhstan | 7500 lambs | Echinococcosis |
| Eastern Kazakhstan | 11000 lambs and 200 dogs | Echinococcosis Echinococcosis |
| Eastern Kazakhstan | 1500 lambs | Dictyocaulasis |
| Eastern Kazakhstan | 11700 lambs and 68 dogs | Echinococcosis Echinococcosis |

What is claimed is:

1. A compound for eliciting an anti-hyaluronidase immune response and protecting a vertebrate against infection by a helminth comprising hyaluronidase covalently coupled to an immunostimulating carrier, which covalent couple elicits an anti-hyaluronidase immune response directed against the helminth.

2. A composition in the form of a vaccine including the compound of claim 1 and a pharmaceutically acceptable carrier.

3. The vaccine of claim 2 wherein said immunostimulating carrier is SYNPOL, which is a copolymer of ethylenepiperazine N-oxide and N-ethylacetylethylenepiperazinium bromide.

4. The vaccine of claim 2 wherein said hyaluronidase is selected from the group consisting of hyaluronoglucosaminidases, hyaluronoglucuronidases and glucoronate lyases.

5. The vaccine of claim 4 wherein said hyaluronidase has a specific enzyme activity ranging from about 150 to about 1500 U.S.P.

6. The vaccine of claim 2 which includes an adjuvant.

7. The vaccine of claim 6 wherein said adjuvant comprises aluminum hydroxide.

8. The vaccine of claim 6 wherein said adjuvant comprises a modified muramyldipeptide.

9. The vaccine of claim 4 wherein said hyaluronidase, either naturally or recombinantly produced, is from a source selected from the group consisting of a cow, a sheep, a leech, bee venom, snake venom, a bacterium, a yeast, and a mammalian cell.

Figure 5:
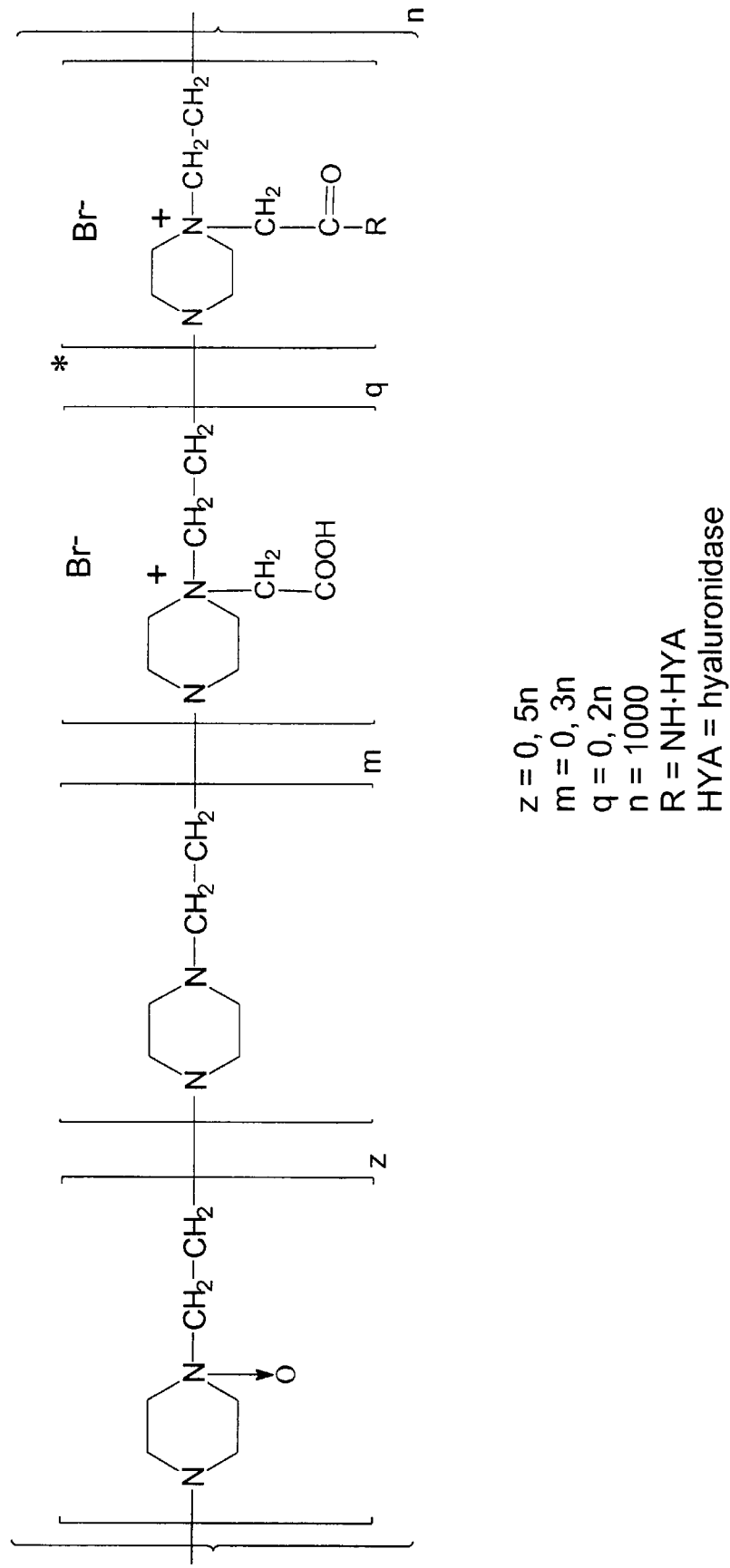
FIG. 5 shows a covalent conjugate of hyaluronidase and SYNPOL 1000-20/50.

10. The vaccine of claim 3 wherein the covalent couple is of the formula as shown in FIG. 5.

11. A process for protecting a vertebrate against infection by a helminth which comprises administering to the vertebrate a therapeutically effective amount of a compound comprising hyaluronidase covalently coupled to an immunostimulating carrier, and eliciting an anti-hyaluronidase immune response directed against the helminth.

12. The process of claim 11, wherein said compound is administered to the vertebrae in the form of a vaccine.

13. The process of claim 11 wherein said immunostimulating carrier is SYNPOL, which is a copolymer of ethylenepiperazine N-oxide and N-ethylacetylethylenepiperazinium bromide.

14. The process of claim 12 where said hyaluronidase is selected from the group consisting of hyaluronoglucosaminidases, hyaluronoglucuronidases and glucoronate lyases.

15. The process of claim 14 wherein said hyaluronidase has a specific enzyme activity ranging from about 150 to about 1500 U.S.P.

16. The process of claim 12 wherein said vaccine includes an adjuvant.

17. The process of claim 16 wherein said adjuvant comprises aluminum hydroxide.

18. The process of claim 16 wherein said adjuvant comprises a modified muramyldipeptide.

19. The process of claim 11 wherein said therapeutically effective amount comprises about 0.05 mg per kg. of body weight of said vertebrate.

20. The process of claim 11 wherein said vertebrate is selected from the group consisting of man, cattle, sheep, swine, dogs, horses, cats, goats, buffaloes, camelidae and poultry.

21. The process of claim 14 wherein said hyaluronidase, either naturally or recombinantly produced, is from a source selected from the group consisting of a cow, a sheep, a leech, bee venom, snake venom, a bacterium, a yeast, and a mammalian cell.

22. The process of claim 13 wherein the covalent couple is of the formula as shown in FIG. 5.

23. A process for eliciting an anti-hyaluronidase immune response in a vertebrate to a helminth which comprises administering to said vertebrate a compound comprising hyaluronidase covalently coupled to an immunostimulating carrier.

24. The process of claim 23 wherein said compound is administered to said vertebrate in the form of a vaccine.

25. The process of claim 24 wherein said immunostimulating carrier is SYNPOL, which is a copolymer of ethylenepiperazine N-oxide and N-ethylacetylethylenepiperazinium bromide.

26. The process of claim 24 wherein said hyaluronidase is selected from the group consisting of hyaluronoglucosaminidases, hyaluronoglucruronidases and glucoronate lyases.

27. The process of claim 26 wherein said hyaluronidase has a specific enzyme activity ranging from about 150 to about 1500 U.S.P.

28. The process of claim 24 wherein said vaccine includes an adjuvant.

29. The process of claim 28 wherein said adjuvant comprises aluminum hydroxide.

30. The process of claim 28 wherein said adjuvant comprises a modified muramyldipeptide.

31. The process of claim 26 wherein said hyaluronidase, either naturally or recombinantly produced, is from a source selected from the group consisting of a cow, a sheep, a leech, bee venom, snake venom, a bacterium, a yeast, and a mammalian cell.

32. The process of claim 25 wherein the covalent couple is of the formula as shown in FIG. 5.

33. A composition comprising the reaction product of hyaluronidase and an immunostimulating carrier, wherein the immunostimulating carrier is SYNPOL.

34. The product of claim 33 having the formula as shown in FIG. 5.

35. A compound for eliciting an immune response to hyaluronidase which comprises hyaluronidase covalently conjugated to an immunostimulatory carrier which is SYNPOL, which is a copolymer of ethylenepiperazine N-oxide and N-ethylacetyl-ethylenepiperazinium bromide.

36. The compound of claim 35 wherein the conjugate is of the formula as shown in FIG. 5.

37. A method of eliciting an anti-hyaluronidase immune response in a mammal which comprises administering to said mammal a compound which comprises hyaluronidase conjugated to an immunostimulatory carrier which is SYNPOL, which is a copolymer of ethylenepiperazine N-oxide and N-ethylacetylethylenepiperaziniumbromide, which conjugate is of the formula as shown in FIG. 5.

38. A vaccine composition for eliciting an anti-hyaluronidase immune response and protecting a mammal against infection by a helminth, which vaccine comprises hyaluronidase conjugated to an immunostimulatory carrier which is SYNPOL, which is a copolymer of ethylenepiperazine N-oxide and N-ethylacetylethylenepiperaziniumbromide and a pharmaceutically acceptable carrier.

39. The vaccine of claim 38 wherein the copolymer is of the formula as shown in FIG. 1.

40. The vaccine of claim 39 wherein $q=0.35$, $z=0.60$, $m=0.05$ and $n=1000$.

41. The vaccine of claim 39 wherein $q=0.2$, $z=0.5$, $m=0.3$ and $n=1000$.

42. The method of claim 37, wherein hyaluronidase is conjugated to an immunostimulatory carrier which is SYNPOL, which is a copolymer of ethylenepiperazine N-oxide and N-ethylacetylethylenepiperazinium bromide, which conjugate is of the formula as shown in FIG. 5.

* * * * *

UNITED STATES PATENT AND TRADEMARK OFFICE
CERTIFICATE OF CORRECTION

PATENT NO. : 5,811,100
DATED : September 22, 1998
INVENTOR(S) : Daugalieva et al.

Page 1 of 1

It is certified that error appears in the above-identified patent and that said Letters Patent is hereby corrected as shown below:

<u>Column 49, claim 3,</u>
Lines 58-59, "ethyleneiperazine" should read -- ethylenepiperazine --.

<u>Column 50, claim 12,</u>
Line 33, "vertebrae" should read -- vertebrate --.

<u>Column 51, claim 26,</u>
Line 9, "hyaluronoglucruronidases" should read -- hyaluronoglucuronidases --.

<u>Column 52, claim 37,</u>
Lines 11-12, "N-ethylacetylethylenepiperaziniumbromide, which conjugate is of the formula as shown in FIG. 5." should read -- N-ethylacetylethylenepiperazinium bromide. --.

Signed and Sealed this

Twenty-sixth Day of March, 2002

Attest:

JAMES E. ROGAN
*Attesting Officer*    *Director of the United States Patent and Trademark Office*